(12) United States Patent
Fung et al.

(10) Patent No.: US 9,398,875 B2
(45) Date of Patent: Jul. 26, 2016

(54) METHOD AND SYSTEM FOR BIOLOGICAL SIGNAL ANALYSIS

(71) Applicant: Honda Motor Co., Ltd., Tokyo (JP)

(72) Inventors: Kin C. Fung, Dublin, OH (US);
Timothy J. Dick, Dublin, OH (US);
Charles William Hall, Jr., Hilliard, OH (US)

(73) Assignee: Honda Motor Co., Ltd., Tokyo (JP)

( * ) Notice: Subject to any disclaimer, the term of this patent is extended or adjusted under 35 U.S.C. 154(b) by 379 days.

(21) Appl. No.: 14/074,710

(22) Filed: Nov. 7, 2013

(65) Prior Publication Data
US 2015/0126818 A1  May 7, 2015

(51) Int. Cl.
A61B 5/00 (2006.01)
A61B 5/18 (2006.01)
A61B 5/024 (2006.01)
A61B 5/08 (2006.01)

(52) U.S. Cl.
CPC .............. *A61B 5/18* (2013.01); *A61B 5/02405* (2013.01); *A61B 5/02444* (2013.01); *A61B 5/0816* (2013.01); *A61B 5/6822* (2013.01); *A61B 5/6823* (2013.01); *A61B 5/6893* (2013.01); *A61B 5/7225* (2013.01); *A61B 2560/0462* (2013.01); *A61B 2562/0204* (2013.01); *A61B 2562/046* (2013.01)

(58) Field of Classification Search
CPC .................. A61B 5/0002–5/0024; A61B 5/18; A61B 5/02; A61B 5/024; A61B 5/02405; A61B 5/02444
See application file for complete search history.

(56) References Cited

U.S. PATENT DOCUMENTS

| | | | |
|---|---|---|---|
| 6,575,902 B1 | 6/2003 | Burton | |
| 7,496,457 B2 | 2/2009 | Fujita et al. | |
| 8,251,447 B2 | 8/2012 | Fujita et al. | |
| 2004/0032957 A1 | 2/2004 | Mansy et al. | |
| 2004/0088095 A1 | 5/2004 | Eberle et al. | |
| 2005/0155808 A1 | 7/2005 | Braeuchle et al. | |
| 2006/0283652 A1 | 12/2006 | Yanai et al. | |
| 2007/0159344 A1 | 7/2007 | Kisacanin | |
| 2011/0034912 A1 | 2/2011 | De Graff et al. | |
| 2011/0152701 A1 | 6/2011 | Buxi et al. | |
| 2012/0022392 A1 | 1/2012 | Leuthardt et al. | |
| 2012/0259181 A1 | 10/2012 | Fujita et al. | |

(Continued)

FOREIGN PATENT DOCUMENTS

WO 2009104460 8/2009

OTHER PUBLICATIONS

International Search Report and Written Opinion of PCT/US2015/037019 dated Nov. 2, 2015, 12 pages.

(Continued)

*Primary Examiner* — Scott Getzow
(74) *Attorney, Agent, or Firm* — Rankin, Hill & Clark LLP

(57) ABSTRACT

A method for biological signal analysis, including providing a multidimensional sensor array disposed at a position for sensing biological data associated with a person, wherein the multidimensional sensor array includes a plurality of sensors and each sensor of the plurality of sensors is mechanically coupled to a common structural coupling material. The method including selectively receiving an output from each sensor of the plurality of sensors, processing the output from each sensor of the plurality of sensors and outputting a biological signal based on the processing.

19 Claims, 16 Drawing Sheets

(56) References Cited

U.S. PATENT DOCUMENTS

2012/0290215 A1 11/2012 Adler et al.
2013/0030256 A1 1/2013 Fujita et al.
2013/0245886 A1 9/2013 Fung et al.

OTHER PUBLICATIONS

Extended European Search Report of EP Serial No. 14 189 710.8 dated Jan. 27, 2015, 9 pages.

METHOD AND SYSTEM FOR BIOLOGICAL SIGNAL ANALYSIS

BACKGROUND

Indicators of aortic blood flow, average heart rate, heart rate variability and beat-to-beat interval can be used to infer levels of sympathetic and parasympathetic nervous system activity, collectively referred to as autonomic tone. An individual's level of autonomic tone is associated with a level of arousal. When used in the context of a vehicle, estimation of autonomic tone of a driver can indicate suboptimal levels of arousal and therefore can be used to detect driver impairment.

Different vehicle interfaces exist to determine autonomic tone of a driver in a vehicle. For example, an interface can acquire different biological signals (e.g., indicating aortic blood flow, average heart rate, heart rate variability and beat-to-beat interval.) from a driver and analyze the biological signals to determine an estimation of autonomic tone. The vehicle environment, specifically, noise and vibrations from engine idling, road travel, among other sources, can interfere with the acquisition and analysis of biological signals in the vehicle and therefore influence the estimation of autonomic tone.

BRIEF DESCRIPTION

According to one aspect, a method for biological signal analysis includes providing a multidimensional sensor array disposed at a position for sensing biological data associated with a person, wherein the multidimensional sensor array includes a plurality of sensors, wherein each sensor of the plurality of sensors is mechanically coupled to a common structural coupling material. The method also includes selectively receiving an output from each of the plurality of sensors, processing the output from each sensor of the plurality of sensors and outputting a biological signal based on the processing.

According to another aspect, a system for biological signal analysis includes a multidimensional sensor array disposed at a position for sensing biological data associated with a person, wherein the multidimensional sensor array includes a plurality of sensors, wherein each sensor of the plurality of sensors is mechanically coupled to a common structural coupling material. The system also includes a filter for selectively receiving an output from each of the plurality of sensors, processing the output from each of the plurality of sensors and outputting a biological signal based on the processing.

According to a further aspect, a non-transitory computer-readable storage medium storing instructions that, when executed by a computer, causes the computer to perform the steps of receiving an output from a multidimensional sensor array that is disposed in a position for sensing biological data associated with a person, wherein the multidimensional sensor array includes a plurality of sensors, wherein each of the sensors of the plurality of sensors is mechanically coupled to a common structural coupling material, selectively forwarding an output from each sensor of the plurality of sensors and outputting a biological signal based on the processing.

According to another aspect, a multidimensional sensor arrangement for biological signal analysis includes a plurality of sensors and a common structural coupling material upon which each sensor of the plurality of sensors is mechanically fixed. The arrangement includes a filter operatively connected to the plurality of sensors, the filter configured to selectively receive output from each of the plurality of sensors and process the output, thereby outputting a biological signal.

DETAILED DESCRIPTION

Figure 1:
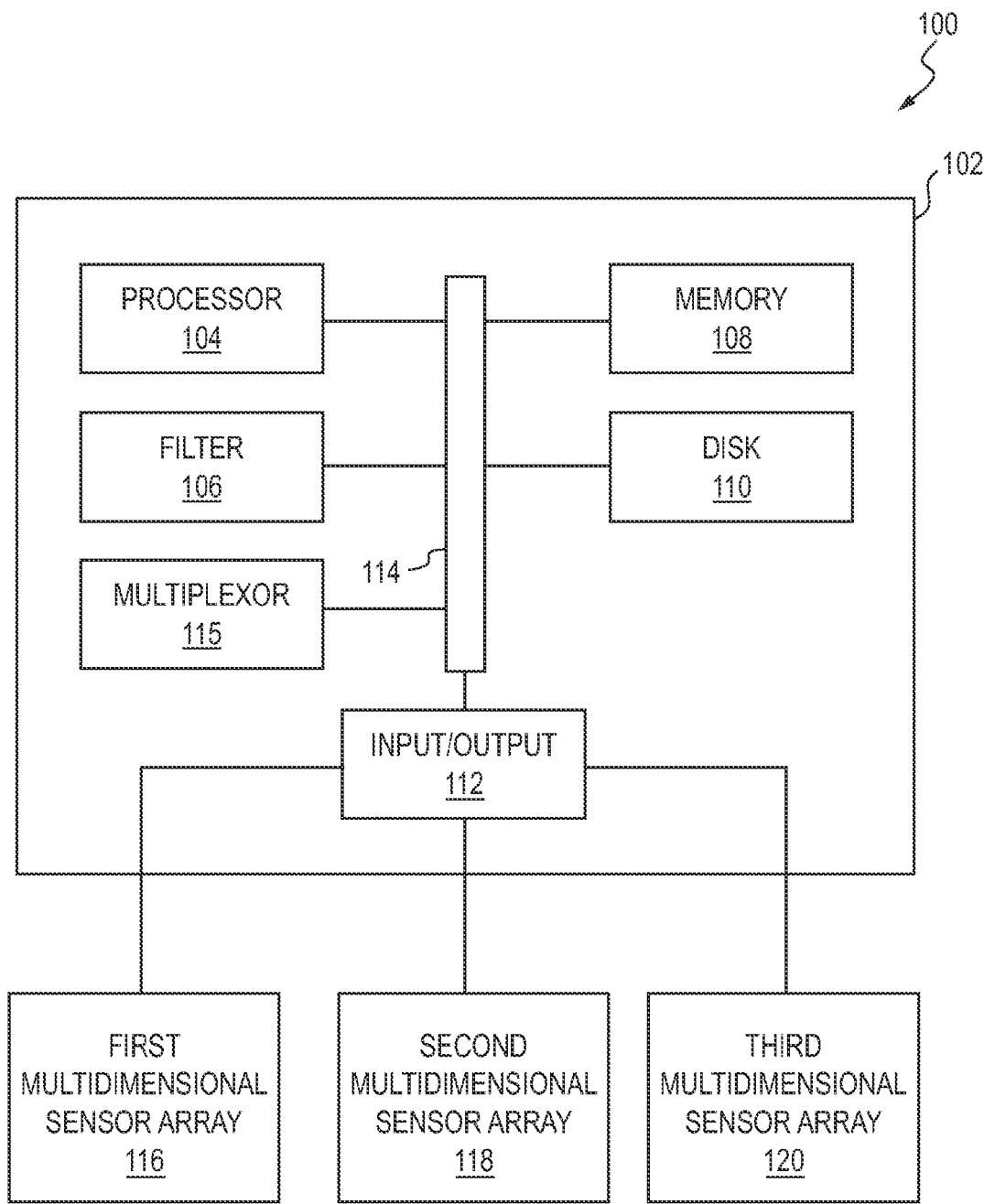
FIG. 1 is a schematic view of a system for biological signal analysis according to an exemplary embodiment.

The embodiments described herein include definitions of selected terms employed herein. The definitions include various examples and/or forms of components that fall within the scope of a term and that can be used for implementation. The examples are not intended to be limiting. Further, one having ordinary skill in the art will appreciate that the components discussed herein, can be combined, omitted or organized with other components or into organized into different architectures. Additionally, headings are used herein and are not intended to be limiting, rather, the headings are provided for structure and organization of explanations and examples.

A "bus", as used herein, refers to an interconnected architecture that is operably connected to other computer components inside a computer or between computers. The bus can transfer data between the computer components. The bus can be a memory bus, a memory controller, a peripheral bus, an external bus, a crossbar switch, and/or a local bus, among others. The bus can also be a vehicle bus that interconnects components inside a vehicle using protocols such as Controller Area network (CAN), Local Interconnect Network (LIN), among others.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "memory", as used herein can include volatile memory and/or nonvolatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDRSDRAM), and direct RAM bus RAM (DRRAM). The memory can store an operating system that controls or allocates resources of a computing device.

A "module", as used herein, includes, but is not limited to, hardware, firmware, software in execution on a machine, and/or combinations of each to perform a function(s) or an action(s), and/or to cause a function or action from another module, method, and/or system. A module can include a software controlled microprocessor, a discrete logic circuit, an analog circuit, a digital circuit, a programmed logic device, a memory device containing executing instructions, and so on.

An "operable connection", or a connection by which entities are "operably connected", is one in which signals, physical communications, and/or logical communications can be sent and/or received. An operable connection can include a physical interface, a data interface and/or an electrical interface.

A "processor", as used herein, processes signals and performs general computing and arithmetic functions. Signals processed by the processor can include digital signals, data signals, computer instructions, processor instructions, messages, a bit, a bit stream, or other means that can be received, transmitted and/or detected. Generally, the processor can be a variety of various processors including multiple single and multicore processors and co-processors and other multiple single and multicore processor and co-processor architectures. The processor can include various modules to execute various functions.

A "vehicle", as used herein, refers to any machine capable of carrying one or more human occupants and is powered by any form of energy. The term "vehicle" includes, but is not limited to: cars, trucks, vans, minivans, airplanes, all-terrain vehicles, multi-utility vehicles, lawnmowers and boats.

A "seat," as used herein refers to any device that can be sat upon or laid upon by a person. The term "seat" includes, but is not limited to: chairs, couches, beds, benches and vehicle seats.

I. System for Biological Signal Analysis

Referring now to the drawings, wherein the showings are for purposes of illustrating one or more exemplary embodiments and not for purposes of limiting same, FIG. 1 illustrates a system 100 for biological signal analysis according to one exemplary embodiment. The system 100 illustrated in FIG. 1 can be implemented alone or in combination with a computing device 102 (e.g., a controller, a navigation system, an infotainment system, etc.). It is to be appreciated that the components of system 100, as well as the components of other systems and architectures discussed herein, can be combined, omitted or organized into different architectures for various embodiments.

In the illustrated embodiment of FIG. 1, the computing device 102 includes a processor 104, a filter 106, a memory 108, a disk 110 and an input/output (I/O) interface 112, which are operably connected for computer communication via a bus 114 and/or other wired and wireless technologies. In one embodiment, the computing device 102 also includes a multiplexor 115. It will be appreciated that in one embodiment, the filter 106 can include the multiplexor 115. In another embodiment, the multiplexor 115 can be implemented externally from of the filter 106 and/or the computing device 102. In a further embodiment, the I/O interface 112 can include the multiplexor 115. It will be appreciated that other vehicle components and systems can be implemented within or operably connected to the computing device 102, however, for purposes of simplicity, these components are not shown in FIG. 1. Further, it is to be appreciated that the computing system 102 can be operably connected for computer communication to other networks and data sources, for example, the Internet, a cellular network, among others (not shown). The I/O interface 112 provides software and hardware to facilitate data input and output between the components of the computing device 102 and other networks and data sources. As described herein, the system 100 can be implemented in various configurations and embodiments, for example, in seats, vehicles or other similar embodiments, where it may be desired to detect a biological signal.

In the illustrated embodiment of FIG. 1, the system 100 also includes a multidimensional sensor array 116. In another exemplary embodiment, the system 100 includes more than one multidimensional sensor array. For example, in the illustrated embodiment shown in FIG. 1, the system 100 can include a second multidimensional sensor array 118 and a third multidimensional sensor array 120. It will be appreciated that the systems and methods discussed herein can be implemented with any number of multidimensional sensor arrays (e.g., two multidimensional sensor arrays or more than three multidimensional sensor arrays). Further, although some embodiments and examples discussed herein refer to the multidimensional sensor array 116, it will be appreciated that the second multidimensional array 118 and the third multidimensional array 120 provide similar functionality as the multidimensional sensor array 116.

A. Multidimensional Sensor Array

Figure 2:
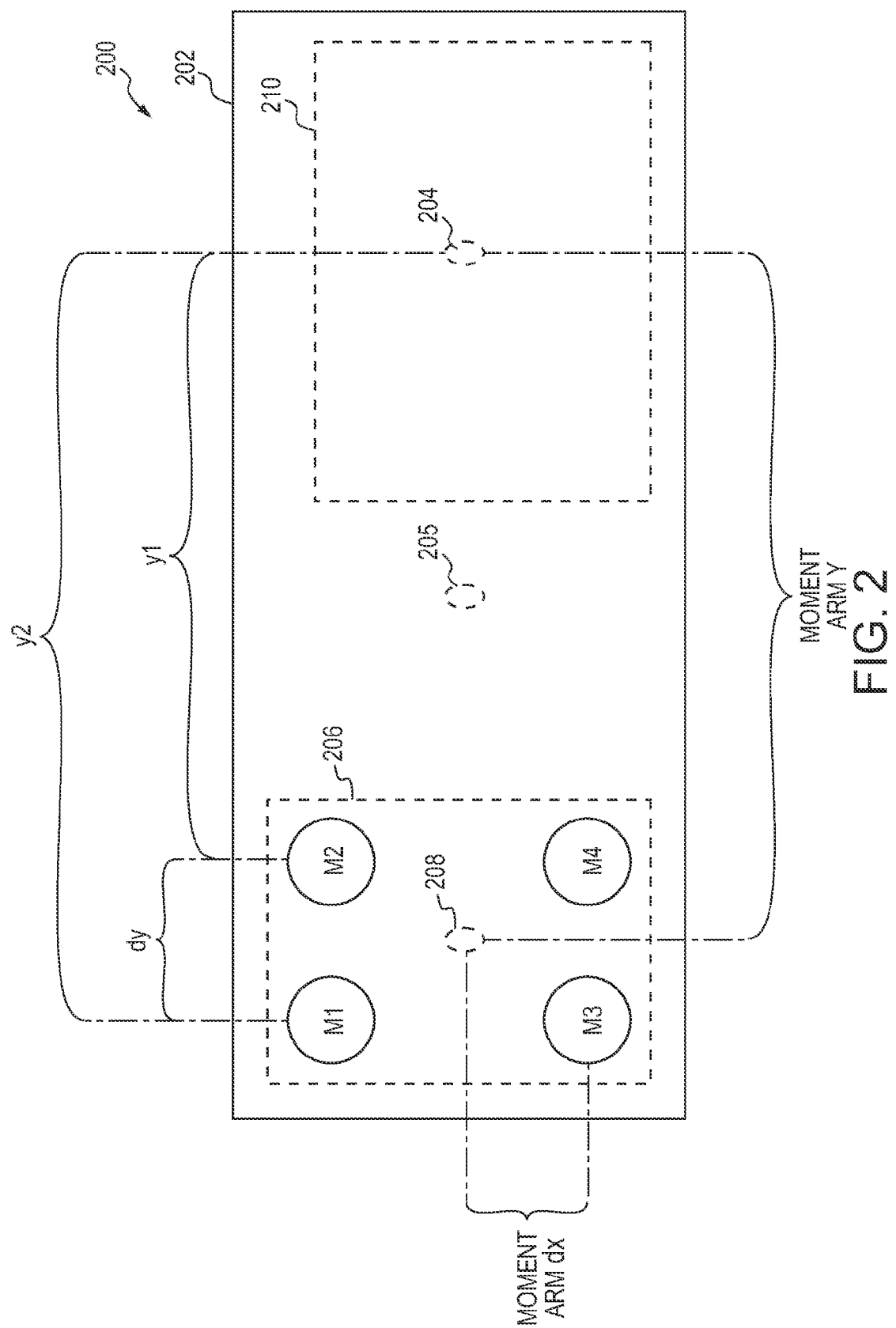
FIG. 2 is a top schematic view of a multidimensional sensor array implemented in the system of FIG. 1 according to an exemplary embodiment.

The multidimensional sensor array 116 will now be described in further detail and with regard to an embodiment associated with a vehicle. It should be noted that another embodiment could be applied to a seat outside a vehicle, such as a chair or a bed. The multidimensional sensor array 116 is disposed at a position for sensing biological data associated with a driver. The position of the multidimensional sensor array 116 will be described below within the context of a vehicle (FIG. 4). The multidimensional sensor array 116 includes a plurality of sensors each of which are mechanically coupled to a common structural coupling material. FIG. 2 illustrates a top schematic view of an exemplary multidimensional sensor array (e.g., the multidimensional sensor array 116, the second multidimensional 118 and/or the third multidimensional sensor array 120) generally shown by reference numeral 200. Similarly, FIG. 3 illustrates an orthographic view of the multidimensional sensor array of FIG. 2.

Figure 3:
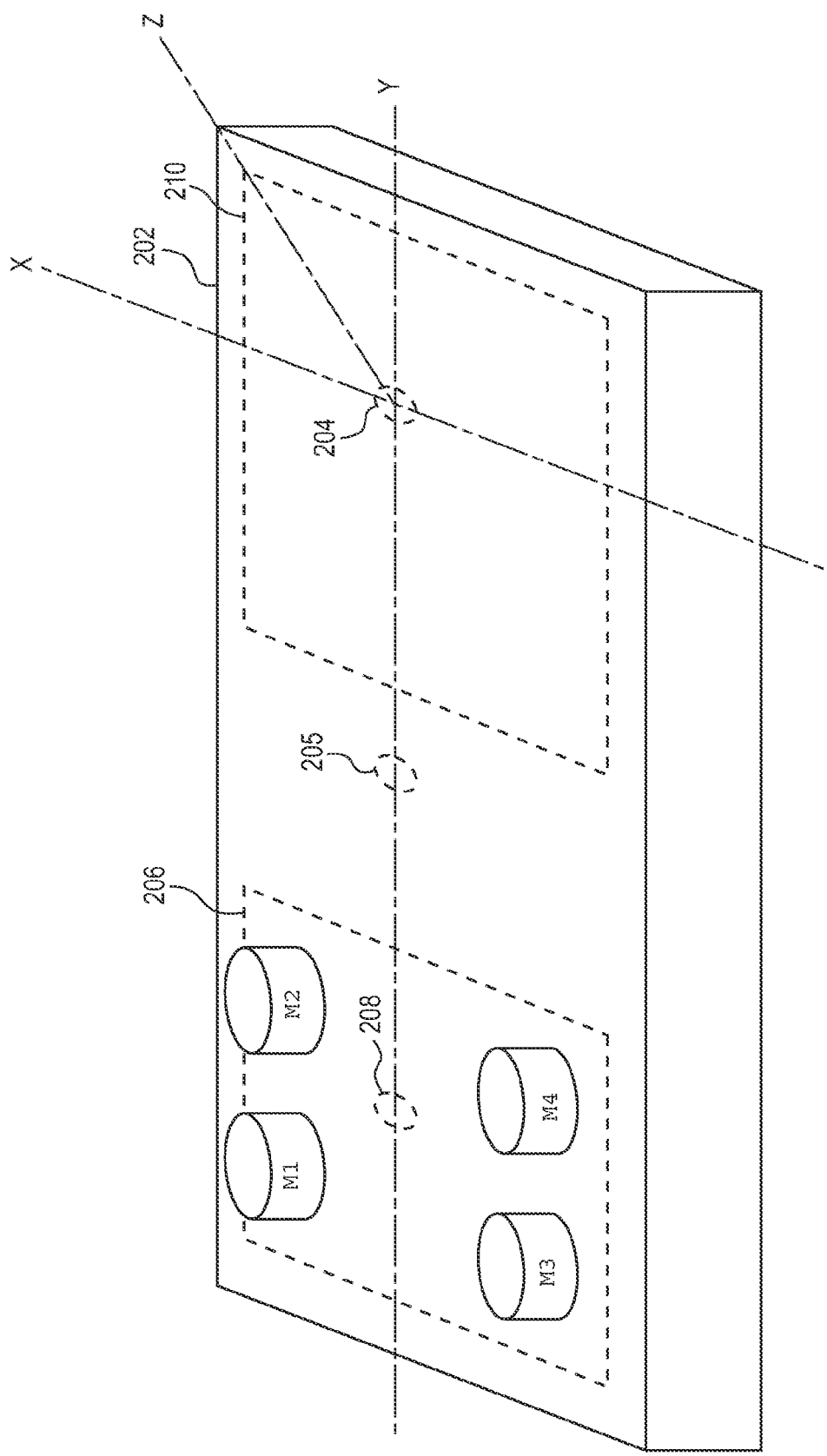
FIG. 3 is an orthographic view of the multidimensional sensor array of FIG. 2.
Figure 4:
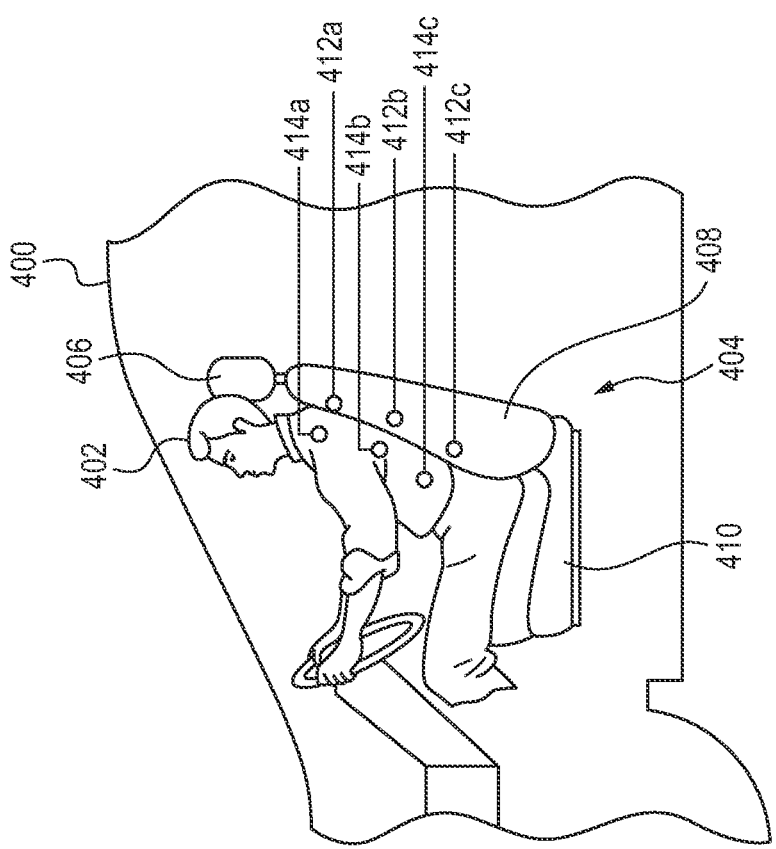
FIG. 4 is a schematic view of the system of FIG. 1 implemented in a vehicle according to an exemplary embodiment.

As is shown in FIGS. 2 and 3, the multidimensional sensor array 200 includes a plurality of sensors M1, M2, M3 and M4. It will be appreciated that in some embodiments, the multidimensional sensor array 200 can include other numbers of sensors, for example, two sensors or more than four sensors. In the embodiment illustrated in FIG. 2, the sensors M1, M2, M3 and M4 are acoustic sensors, for example, microphones. Accordingly, the sensors M1, M2, M3 and M4 are configured to sense an acoustic measurement (e.g., a stimulus) of biological data associated with a person and generate a data stream or a raw data signal (e.g., output) representing the acoustic measurement. Biological data can include, but is not limited to, data associated with the heart (e.g., aortic blood flow, average heart rate, heart rate variability and beat-to-beat interval), the lungs (e.g., respiratory rate) and other biological systems of the human body.

In the illustrated embodiment of FIG. 2, the sensors M1, M2, M3 and M4 are mechanically coupled to a common structural coupling material 202. The common structural coupling material 202 provides a connection in a non-electrical manner between the sensors M1, M2, M3 and M4. The mechanical coupling allows for distribution of ambient mechanical vibrations (e.g., engine noise, road noise) equally to each of the sensors M1, M2, M3 and M4. In one embodiment, the common structural coupling material 202 is a circuit board upon which the sensors M1, M2, M3 and M4 are fixed (e.g., via adhesives, bonding, pins). In another embodiment, the common structural coupling material 202 is a bracket or includes one or more brackets upon which the sensors M1, M2, M3 and M4 are fixed (e.g., via adhesives, bonding, pins). It will be appreciated that other materials can be used as the common structural coupling material 202. In particular, other materials with a high modulus of elasticity and a low density can be used as the common structural coupling material 202.

By mechanically coupling the acoustic sensors M1, M2, M3 and M4 to a common structural coupling material 202, ambient mechanical vibrations from, for example, the external environment impacts each sensor M1, M2, M3 and M4 equally. As an illustrative example in the context of a vehicle (FIG. 4), vibrations from the vehicle environment (e.g., engine noise, road noise), impact each sensor M1, M2, M3 and M4 equally due to the mechanical coupling provided by the common structural coupling material 202. When the output (e.g., raw signals) from sensors M1, M2, M3 and M4 are processed and/or filtered, as will later be discussed), the vibrations can be eliminated from the raw signals as a common mode.

The configuration of the multidimensional array will now be discussed in more detail. As shown in FIG. 2, the multidimensional array 200 has a geometric center 205 and a center of mass 204. The center of mass 204 is located external to an area bounded by the plurality of sensors. Specifically, the sensors M1, M2, M3 and M4, which are mechanically coupled to the common structural coupling material 202, are provided (i.e., positioned) so as to define the center of mass 204 external to the area bounded by the plurality of sensors. Specifically, the center of mass 204 is located external to an area 206, which is an area bounded by the sensors M1, M2, M3 and M4. The area 206 is defined by a position of each of the plurality of sensors M1, M2, M3 and M4 and a geometric center 208 of the plurality of sensors M1, M2, M3 and M4. In one embodiment, the center of mass 204 is created by a weighted portion 210 of the multidimensional array 200. The weighted portion 210, in one embodiment, is implemented by a power source (not shown) positioned on the multidimensional array 200. In a further embodiment, the center of mass 204 is created by providing the multidimensional array in a curved shape configuration (not shown). By providing the center of mass 204 at a location external to the geometric center 208 of the plurality of sensors M1, M2, M3 and M4, the ambient mechanical vibration (i.e., noise) registers in each of the plurality of sensors M1, M2, M3 and M4, in plane (i.e., in phase) with respect to each other.

More specifically, ambient mechanical vibrations are transferred from the vehicle to the multidimensional array 200. Generally, the ambient mechanical vibrations manifest as linear motion along a horizontal axis (X) direction and a vertical axis (Y) direction of the multidimensional array 200, and in a rotational motion about the horizontal axis (X) and the vertical axis (Y) of the multidimensional array 200. FIG. 3 illustrates a Y, X and Z axes with respect to the multidimensional array 200 and the center of mass 204. The mechanical coupling with respect to each of the sensors M1, M2, M3 and M4, causes each of the sensors M1, M2, M3 and M4 to move in-phase with regards to the vibrational linear motion.

With regards to the vibrational rotational motion, the positioning of each of the sensors M1, M2, M3 and M4 with respect to the center of mass 204 will now be discussed in more detail. Rotational motion about the horizontal (X) axis is proportional to the magnitude of the vibration multiplied by the moment arm Y. As shown in FIG. 2, each of the sensors M1, M2, M3 and M4 define the geometric center 208. The moment arm Y is the vertical distance of the geometric center 208 from the vertical axis (i.e., Y coordinate) of the center of mass 204. Further, a distance y1 is a vertical distance from an axis of the sensors M3, M4 and the center of mass 204 and a distance y2 is a vertical distance from an axis of the sensors M1, M2 and the center of mass 204. By positioning each of the sensors M1, M2, M3 and M4 so that the ratio of dy/Y is small, then y1 is approximately equal to y2 and the ambient mechanical vibrations registered by each of the sensors M1, M2, M3 and M4 are approximately in phase. The ambient mechanical vibrations can then be processed using filtering techniques that will be discussed in further detail herein. Additionally, rotational motion about the vertical (Y) axis is proportional to the magnitude of the vibration multiplied by a moment arm dx. By positioning each of the sensors M1, M2, M3 and M4 so that dx (i.e. the difference between the geometric center 208 and the axis of each of the sensors) is small, the ambient mechanical vibrations registered by each of the sensors M1, M2, M3 and M4 can also be processed using filtering techniques that will be discussed in further detail herein.

Accordingly, in the embodiment illustrated in FIGS. 2 and 3, at least one sensor is positioned along the Y axis with a short and a long moment arm and at least one sensor is positioned along the X axis with an x moment arm on either side of the Y axis. For example, M1 and M2 are positioned along the Y axis with a short and a long moment arm and M3 and M4 are positioned along the X axis with an x moment arm on either side of the Y axis. According to an embodiment described herein, the processing of the output of each of the sensors is based on the sensor pairs (i.e., M2, M3 and M1, M4)

described above. Specifically, the sensors are positioned so that during processing, which is discussed herein, operational amplification adds the motions with the moment arm dx in out of phase combinations. Thus, M1 and M4 are positioned on opposite sides of the Y axis and M2 and M3 are positioned on opposite sides of the Y axis. This allows each additive pair to consist of one sensor moving in each direction about the Y axis with moment arm dx allowing for cancellation using common mode with differential amplification. If both sensors in a pair are on the same side of the Y axis, the rotary noise from rotation about the Y axis with moment X will not cancel with differential amplification but will double instead because they are 180 degrees out of phase before subtraction.

Referring again to FIG. 2, in one embodiment, the multidimensional sensor array further includes one or more clusters. Each of the plurality of sensors M1, M2, M3 and M4 of the multidimensional sensor array 200 can be associated with the one or more clusters. For example, in the illustrated embodiment of FIG. 2, the area 206 can be considered a cluster in which sensors M1, M2, M3 and M4 are associated. In another embodiment, which will be discussed herein, sensors M1 and M3 can be associated with a first cluster and sensors M3 and M4 can be associate with a second cluster. It will be appreciated that the multidimensional sensor array 200 can include any number of clusters (e.g., one cluster or more than two clusters). The clusters may or may not be associated with a specific location (e.g., position) of the sensor on the common structural coupling material 202. Further, the clusters can be predefined and associated with any combination of sensors.

Non-limiting examples of clusters and sensors associated with said clusters will now be discussed. In one embodiment, a sensor array, including more than one sensor, can be associated with a cluster. In a further embodiment, the clusters can be a pattern of sensors or an array of sensors (as discussed above). In another embodiment, the clusters are predefined based on the position of the sensors or the output of the sensors. In an additional embodiment, which will be described herein, the multiplexor 115, can determine the clusters based on a location of the multidimensional array, a location of each sensor in the multidimensional array, and/or the output (e.g., the raw data signal output) of each sensor. Further, a cluster can be determined and/or a sensor can be associated with a cluster based on the positioning of the sensors. In one embodiment, a cluster can include at least one sensor positioned along the Y axis with a short and long moment arm and at least one sensor position along the X axis with an x moment arm on either side of the Y axis. Thus, with reference to FIG. 2, a first cluster can include M2, M3 and a second cluster can include M1, M4. It will be appreciated that other combinations and sensor pairs can be associated with a cluster.

B. Vehicular Context

The multidimensional array 116 and the system 100 of FIG. 1, will now be described in the context of a vehicle 400 in FIG. 4. In one embodiment, the system 100 of FIG. 1 can be used for biological signal analysis of a driver 402 to thereafter determine an arousal level or autonomic tone of the driver 402. The driver 402 can be seated in a vehicle seat 404 of the vehicle 400. The seat 404 includes a headrest 406, a backrest 408 and a seat base 410, although other configurations of the seat 404 are contemplated. Further, the seat 404 can also include a seat belt (not shown). In the embodiment illustrated in FIG. 4, the elements 412a, 412b, 412c indicate positions for sensing biological data associated with the driver 402. Specifically, a multidimensional array or more than one multidimensional array (e.g, the multidimensional array 116, the second multidimensional array 118 and/or the third multidimensional array 120) cab be disposed at said positions 412a, 412b, 412c for sensing biological data associated with the driver 402.

In particular, in FIG. 4, the positions 412a, 412b, 412c are located within the backrest 408. However, it will be appreciated, the positions can be in other areas of the seat 404 (e.g., seat belt (not shown)) or around the seat 404 to allow the multidimensional array disposed at said position to sense biological data associated with the driver 402. For example, in one embodiment, the multidimensional sensor array is disposed at a position for sensing biological data associated with a thoracic region of the driver occupying the vehicle. In FIG. 4, the elements 414a, 414b, 414c indicate thoracic regions of the driver 302. Specifically, the elements 414a, 414b, 414c indicate an upper cervico-thoracic region, a middle thoracic region and a lower thoraco-lumbar region respectively of the thorax of the driver 402. Accordingly, in FIG. 4, the element 412a indicates a position at which a multidimensional sensor array is disposed, wherein the position is proximate to an upper cervico-thoracic region 414a of the driver 402. Additionally, the element 412b indicates a position at which a multidimensional sensor array is disposed, wherein the position is proximate to a middle thoracic region 414b of the driver 402. Further, the element 412c indicates a position at which a multidimensional sensor array is disposed, wherein the position is proximate to a lower thoraco-lumbar region 414c of the driver 402. It will be appreciated that other positions other than the positions 412a, 412b, 412c can be positions proximate to an upper cervico-thoracic region 414a, a middle thoracic region 414b and/or a lower thoraco-lumbar region 414c. For example, in one embodiment, the multidimensional sensor array can be located in one or more positions in a seat belt (not shown) that are proximate to an upper cervico-thoracic region 414a, a middle thoracic region 414b and/or a lower thoraco-lumbar region 414c of the driver 402. In another embodiment, the position can be proximate to an axillary region.

It will be appreciated that in one embodiment, more than one multidimensional sensor array can be implemented wherein each multidimensional sensor array (e.g., the multidimensional sensor array 116, the second multidimensional sensory array 118, the third multidimensional sensor array 120) is disposed at a different position for sensing biological data associated with a different thoracic region of the driver. As an illustrative example, the multidimensional sensor array 116 can be disposed at a position 412a proximate to an upper cervico-thoracic region 414a of the driver 402 and the second multidimensional sensor array 118 can be disposed at a position 412c proximate to an lower thoraco-lumbar region 414c of the driver 402. Other numbers of multidimensional sensor arrays disposed in other positions or combinations of positions can also be implemented.

Figure 5:
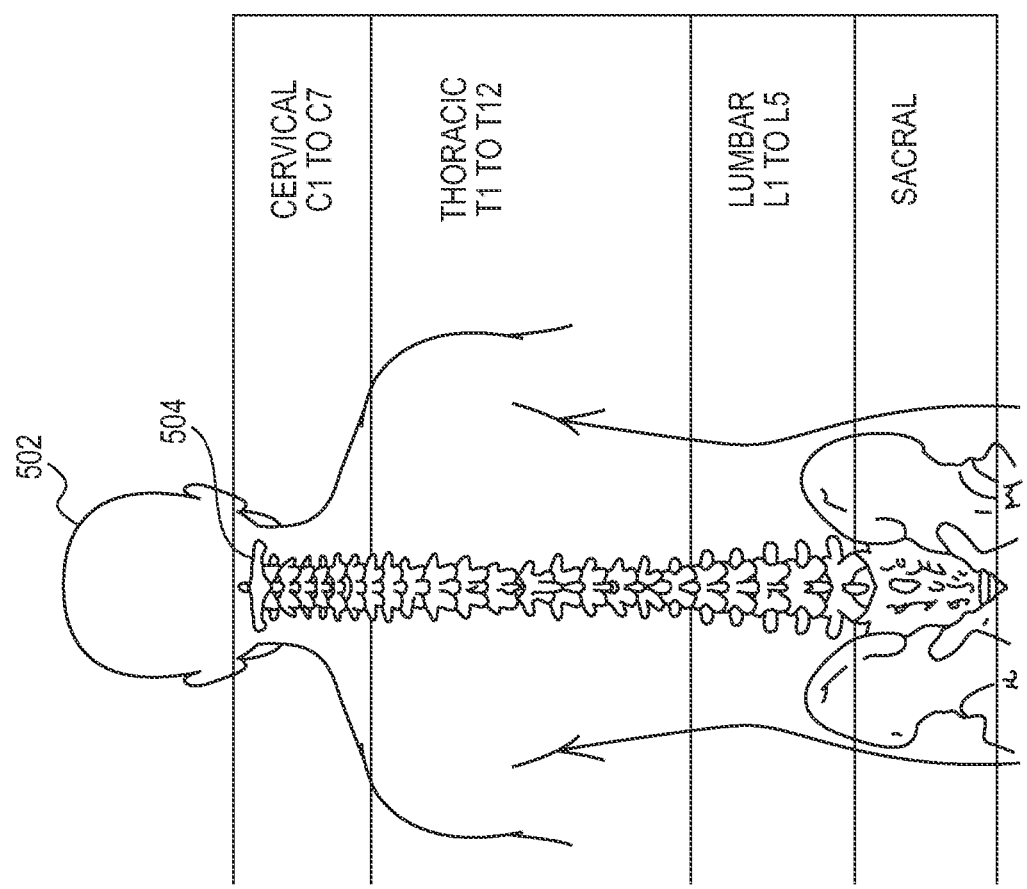
FIG. 5 is a schematic view of exemplary regions of a person.

The upper cervico-thoracic region 414a, the middle thoracic region 414b and the lower thoraco-lumbar region 414c will now be discussed in detail with reference to FIG. 5, a schematic illustration of an individual 502 (e.g., the driver 402) and a vertebral column 504. It will be appreciated that the individual 502 and the vertebral column 504 are based on the anatomy and physiology of an average individual. In one embodiment, the upper cervico-thoracic region 414a corresponds to a cervical region between vertebrae C1 and C7. In another embodiment, the upper cervico-thoracic region 414a corresponds to a thoracic region between vertebrae T1 and T12, for example, between vertebrae T1 and T6. In one embodiment, the middle thoracic region 414b can correspond to a thoracic region between vertebrae T1 and T12, for example, between vertebrae T6 and T12. In another embodiment, the lower thoraco-lumbar region 414c can correspond to a lumbar region between vertebrae L1 and L5. In some embodiments, the upper cervico-thoracic region 414a, the middle thoracic region 414b and the lower thoraco-lumbar region 414c are medial to the vertebral column of the individual 502. It will be appreciated that other regions defined by other vertebral positions can be implemented with the methods and systems discussed herein.

Further, it will be appreciated that one or more multidimensional arrays can be provided and/or disposed at a position for sensing biological data based on the biological data and/or the biological signal. Different positions can correlate with specific biological data or provide the best position for measuring and/or collection of said biological data. For example, a multidimensional array disposed at a position proximate to an upper region 410a can be utilized to obtain a signal associated with heart rate, while a position proximate to a lower region 410c can be utilized to obtain a signal associated with aortic pulse wave. Thus, for example, during processing, the multiplexor 115 can selectively retrieve or obtain output from a sensor or a multidimensional array based on the biological data to be obtained, the position of the multidimensional array and/or a cluster associated with each sensor. Exemplary output from different positions will be discussed in Section 3 with reference to FIGS. 8-16.

C. Processing and Analysis

Referring again to FIG. 1, the filter 106 is generally configured to selectively receive and process an output (e.g., the raw data signal indicating biological data associated with the driver) from each of the plurality of sensors of the multidimensional array 116. It will be appreciated that in some embodiments, the processor 104 and/or the filter 106 can be used alone, or in combination, to provide the hardware and/or the functionality as described herein. Further, in other embodiments, the multidimensional array 116, alone or in combination with the processor 104 and/or the filter 106, can be used to provide the hardware and/or the functionality as described herein. For example, the multidimensional array 116, in one embodiment, can include the processor 104 and/or the filter 106. In another embodiment, the multidimensional array 116 is separate from the processor 104 and/or the filter 106. Further, it will be appreciated that when one or more multidimensional arrays are utilized (e.g., the multidimensional array 116, the second multidimensional array 118 and/or the third multidimensional array 120), the output from each multidimensional array can be processed alone or in combination with the other multidimensional arrays. For example, the second multidimensional array 118 and/or the third multidimensional array 120 can utilize the same filter 106 or utilize different filters that function similarly to the filter 106.

The filter 106 and the multidimensional array 116 will now be described in detail with reference to FIG. 6, which illustrates an exemplary electric circuit diagram 600. It will be appreciated that other electric circuit configurations can be implemented, however, for purposes of simplicity and illustration, the electric circuit diagram 600 has been organized into a sensing portion 602 (e.g., a multidimensional array 116) and a filtering portion 6 (e.g., a processor 104 and/or a filter 106). Further, the electric circuit diagram includes a multiplexor 606 (e.g., the multiplexor 115 in FIG. 1), which can be implemented with the sensing portion 602 and/or the filtering portion 604.

The sensing portion 602 includes acoustic sensors (i.e., microphones) M1, M2, M3 and M4. Similar to FIG. 2, the sensors M1, M2, M3 and M4 are mechanically coupled to a common structural coupling material (not shown in FIG. 6). Although four acoustic sensors are illustrated in FIG. 6, other embodiments can include any number of sensors (e.g., less than four or more than four). In the embodiment illustrated in FIG. 6, each acoustic sensor M1, M2, M3 and M4 is biased at one tenth a supply voltage by a voltage divider circuit formed from resistors R1 and R2 via pull-up resistors Rp1, Rp2, Rp3 and Rp4. In some embodiments, the voltage is supplied to the multidimensional sensor array by a standard DC power supply (not shown). As discussed above with FIG. 2, the standard DC power supply could be implemented as a weighting portion 202. The acoustic sensors M1, M2, M3 and M4 sense an acoustic measurement indicating biological data associated with a driver. The acoustic measurement is determined by the voltage drop between the pull-up resistors Rp1, Rp2, Rp3 and R4 and the associated acoustic sensor to generate an output (e.g., a raw data signal). For example, Vm1 is an output signal indicating a voltage measurement registered by the voltage drop between M1 and Rp1. Vm2 is an output signal indicating a voltage measurement registered by the voltage drop between M2 and Rp2. Vm3 is an output signal indicating a voltage measurement registered by the voltage drop between M3 and Rp3. Vm4 is an output signal indicating a voltage measurement registered by the voltage drop between M4 and Rp4. It will be appreciated that other configurations of voltage biasing and impedance matching can also be implemented with the methods and systems described herein. Further, other types of microphones and/or acoustic sensors, other than electret condenser microphones, can also be implemented. For example, other microphones can include but are not limited to, cardioids, unidirectional, omnidirectional, micro-electromechanical, and piezoelectric. It will be appreciated that other microphones may require different types of biasing and impedance matching configurations.

Figure 6:
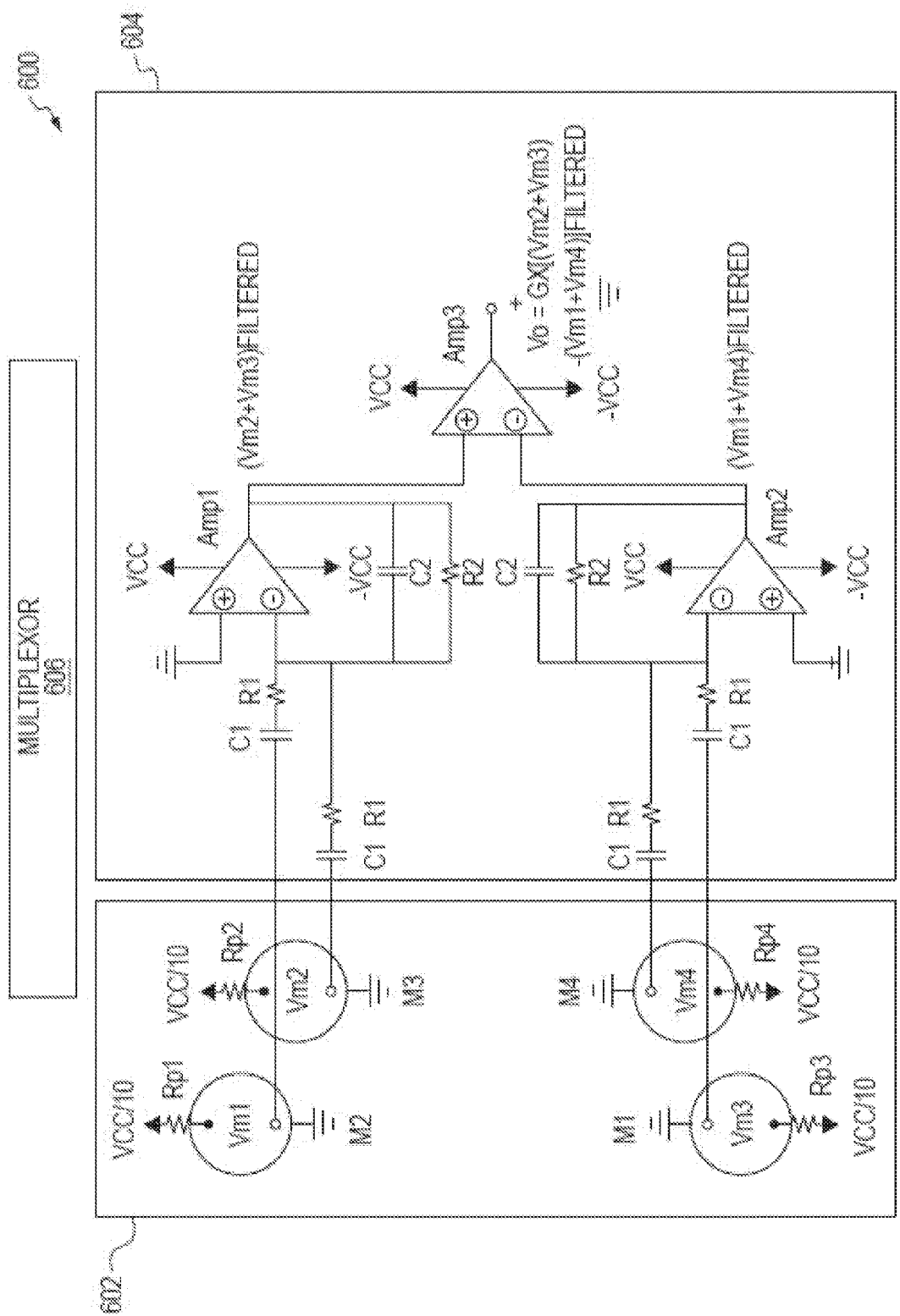
FIG. 6 is an electric circuit diagram of an array of mechanically coupled sensors according to an exemplary embodiment.

In the illustrated embodiment of FIG. 6, each of the plurality of sensors M1, M2, M3 and M4 are associated with one or more clusters. In particular, in FIG. 6, the sensors M2 and M3 are associated with a cluster 608 and the sensors M1 and M4 are associated with a cluster 610. Thus, the cluster 608 includes at least one sensor positioned along the Y axis with a short and long moment arm and at least one sensor position along the X axis with an x moment arm on either side of the Y axis. Similarly, the cluster 610 includes at least one sensor positioned along the Y axis with a short and long moment arm and at least one sensor position along the X axis with an x moment arm on either side of the Y axis.

In one embodiment, the output signals Vm1, Vm2, Vm3 and Vm4 are processed (e.g., via the filtering portion 604) based on the clusters and/or the positioning of each of the sensors. Specifically, the sensors M2 and M3 are connected to one half of an operational amplifier Amp1 via an RC couple R1 and C1. The output signals Vm2 and Vm3 are processed by the Amp 1. Specifically, in this example, the RC couple provides a single pole of high pass filtering at a frequency of 0.34 Hz. The Amp1 is coupled through an output lead via a parallel RC circuit to produce a second pole of low pass filtering at 3.4 Hz with a gain of R2/R1=1 VN. The output of the Amp1 is a summation of the output of M2 and M3, equal to Vm2+Vm3 filtered at 0.34-3.4 Hz.

Similarly, the sensors M1 and M4 are also connected to one half of an operational amplifier Amp2 via an RC couple R1 and C1. The output signals Vm1 and Vm4 are processed by the Amp 2. Specifically, the RC couple provides a single pole of high pass filtering at a frequency of 0.34 Hz. The Amp2 is coupled through an output lead via a parallel RC circuit to produce a second pole of low pass filtering at 3.4 Hz with a gain of R2/R1=1 VN. The output of Amp2 is a summation of the output of M1, M4, equal to Vm1+Vm4 filtered at 0.34-3.4 Hz.

Further, the output of each operational amplifier Amp1, Amp2 is fed to a differential bioinstrumentation amplifier Amp3 configured to deliver a gain of 5000/Rg=50000/10=5000 V/V. The Amp3 can provide noise cancellation of the output of the sensors M1, M2, M3 and M4. In particular, and as discussed above with FIG. 2, due to the mechanical coupling of the sensors M1, M2, M3 and M4, the positioning of the sensors M1, M2, M3 and M4 and the positioning of the center of mass of the multidimensional array, environmental vibrations impact each sensors M1, M2, M3 and M4 equally. Therefore, the Amp3 can remove the environmental vibrations from the output signal of each operational amplifier Amp1, Amp2, as a common mode. The output signal of the differential bioinstrumentation amplifier Amp3 is equal to GX[(Vm2+Vm3)−(Vm1+Vm4)] filtered. The output signal of the differential bioinstrumentation amplifier Amp3 represents a biological signal that can be further analyzed (e.g., by the processor 104) to determine autonomic tone and a level of impairment of the driver 302. With reference to FIG. 2, by adding together sensor pairs containing both a short moment arm y1 and a long moment arm y2 (i.e. Vm2+Vm3 and Vm1+Vm4), the differential effects of the differences in the moment arm become common mode and cancel with differential amplification. Likewise, in choosing sensor pairs in this fashion, the out of plane motion that occurs with rotation about the Y axis with moment arm dx also becomes common mode and cancels out with differential amplification.

As described above, the filter 106 can include various amplifiers (Amp1, Amp2, Amp3) for processing. It will be appreciated that other types of filters and amplifiers can be implemented with the systems and methods discussed herein. For example, band pass filters, phase cancelling filters, among others. It addition to amplification, the filter 106 can include a multiplexor 606 for selectively receiving the output from each of the plurality of sensors and/or selectively forwarding the output from each of the plurality of sensors for processing. In one embodiment, multiplexor 606 can selectively receive and/or obtain an output of a sensor from the plurality of sensors M1, M2, M3, M4 of the multidimensional sensor array 600 for further processing by the Amp1, Amp 2 and/or Amp3 based on a predefined factor. For example, the output can be selected based on a position of a sensor, a position of the multidimensional array, a cluster, a signal to noise ratio of the output, among other factors. In one embodiment, The multiplexor can selectively receive output from a single sensor, more than one sensor from a single cluster or more than one cluster. In another embodiment, the multiplexor 606 can predefine a cluster based on a predefined factor, for example, a position of a sensor, a position of a multiplexor, a signal to noise ratio of the output, among other factors. In an embodiment including more than one multidimensional sensor array, the multiplexor 506 can selectively receive and/or forward output of each of the plurality of sensors from each of the multidimensional sensor array for further processing by the Amp1, Amp 2 and or Amp3 based on a predefined factor. For example, a position of the multidimensional array, a position of a sensor, a signal to noise ratio of the output, among other factors.

Further, in some embodiments, the multiplexor 606 can selectively output to, for example, the processor 104, a biological signal based on a predefined factor for use in algorithms and processes for determining autonomic tone and/or a level of impairment of the driver 402. For example, the biological signal can be outputted based on a signal-to-noise ratio, a biological data type, or a position of the multidimensional array, among others. As can be appreciated, various combinations of output from one or more multidimensional arrays and each of the plurality of sensors are contemplated.

It will be appreciated that other configurations of the system 100 of FIG. 1 can be contemplated. Another embodiment will now be discussed with reference to FIGS. 1-6. In particular, the system 100 will be described as a multidimensional sensor arrangement. The components of FIGS. 1-6 within the context of the multidimensional sensor arrangement function similarly to the components of FIGS. 1-5 discussed above. The multidimensional sensor arrangement (e.g., the system 100) includes a plurality of sensors associated with one or more clusters. For example, in FIG. 1, the multidimensional sensor array 200 includes a plurality of sensors M1, M2, M3 and M4. Each of the sensors M1, M2, M3 and M4 can be associated with one or more clusters, which will be described in more detail herein.

The multidimensional sensor arrangement 100 also includes a common structural coupling material upon which the first plurality of sensors and the second plurality of sensors are mechanically fixed. Again, with reference to FIG. 2, the multidimensional sensor array 200 includes a common structural coupling material 202 upon which each of the sensors M1, M2, M3 and M4 are mechanically fixed. Other types of configurations can also be contemplated. Further, a center of mass of the multidimensional array is located externally to a geometric center defined by the plurality of sensors.

The multidimensional sensor arrangement 100 also includes a filter operatively connected to the plurality of sensors, the filter configured to selectively receive output from each of the plurality of sensors and process the output, thereby outputting a biological signal. For example, in FIG. 6, the filtering portion 604 is operatively connected to the sensors M1 and M2 and the sensors M3 and M4. The filter (i.e., the multiplexor 506) is configured to selectively receive the output and forward the output to the filter (e.g., Amp1, Amp2, Amp3) to process the output. In one embodiment, the filter is configured to process the output based on the cluster associated with each sensor. Thus, as discussed in detail with FIG. 6, the output signals Vm1, Vm2, Vm3 and Vm4 are processed (e.g., the filtering portion 504) based on the cluster associated with each of the plurality of sensors in the multidimensional array. It will be appreciated, that other configurations of the system 100, including the multidimensional sensor arrangement, can be contemplated with the system and methods discussed herein.

II. Method for Biological Signal Analysis

Figure 7:
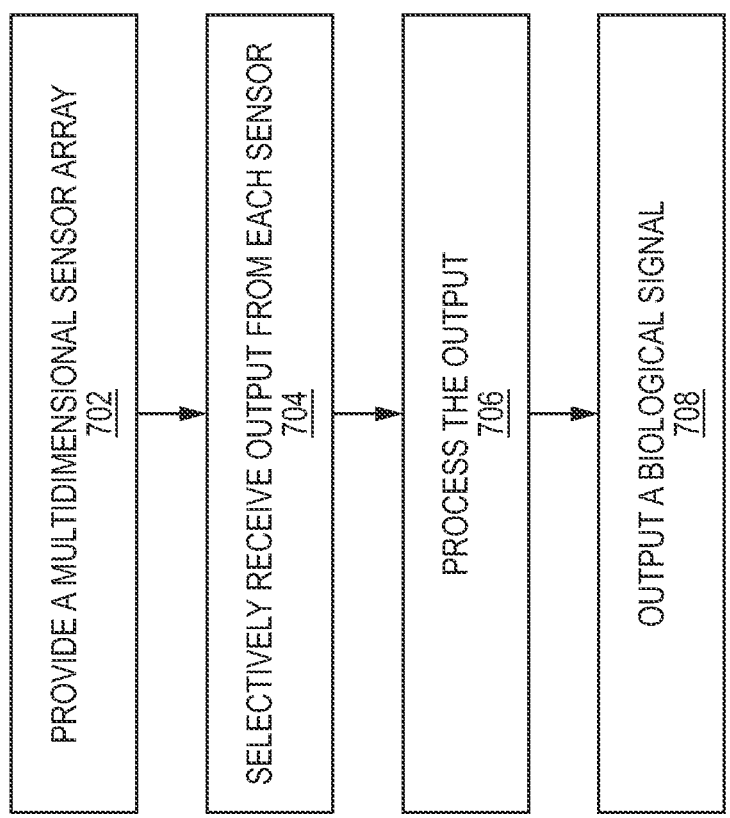
FIG. 7 is a flow chart of a process for biological signal analysis according an exemplary embodiment.

The system of 100 will now be described in operation with reference to a method of FIG. 7. The method of FIG. 6 is described with reference to the systems and components of FIGS. 1-4 and 6, although it is to be appreciated that the method could be used with other systems and components. The method of FIG. 7 includes, at step 702, providing a multidimensional sensor array. For example, in FIG. 1, the system 100 includes a multidimensional sensor array 116. In another embodiment, the system 100 includes one or more multidimensional sensor arrays, for example, the multidimensional sensor array 116, the second multidimensional sensor array 118 and the third multidimensional sensor array 120.

The multidimensional sensor array includes a plurality of sensors mechanically coupled to a common structural coupling material. As discussed above in detail with FIG. 2, the multidimensional sensor array 200 includes a plurality of sensors M1, M2, M3 and M4. In one embodiment, the sensors M1, M2, M3 and M4 are acoustic sensors, for example, microphones. The sensors M1, M2, M3 and M4 are mechanically coupled to a common structural coupling material 202. The common structural coupling material 202 provides a connection in a non-electrical manner between the sensors M1, M2, M3 and M4.

Further, each of the plurality of sensors can be associated with one or more clusters. With reference to FIG. 6, the multidimensional sensor array includes a cluster 608 and a cluster 610. It will be appreciated the multidimensional sensor array 200 can include any number clusters. A cluster is associated with or includes one or more sensors (e.g., M1, M2, M3 and/or M4). For example, in FIG. 6, the sensors M2, and M3 are associated with the cluster 608 and the sensors M1, M4 are associated with the cluster 610. It is appreciated that other configurations and patterns of regional groups can be implemented with the sensors M1, M2, M3 and M4.

Referring again to step 702, the multidimensional sensor array is disposed at a position for sensing biological data associated with a driver. As discussed above in detail with FIG. 4, the elements 412a, 412b, 412c indicate positions at which a multidimensional array or more than one multidimensional array (e.g., the multidimensional array 116, the second multidimensional array 118 and/or the third multidimensional array 120) is disposed for sensing biological data associated with the driver 402. In one embodiment, the multidimensional sensor array is disposed at a position for sensing biological data associated with a thoracic region of the driver occupying the vehicle. In FIG. 4, the elements 414a, 414b, 414c indicate thoracic regions of the driver 402. Specifically, the elements 414a, 414b, 414c indicate an upper cervico-thoracic region, a middle thoracic region and a lower thoraco-lumbar region respectively of the thorax of the driver 402.

It will be appreciated that in one embodiment, more than one multidimensional sensor array can be implemented wherein each multidimensional sensor array (e.g., the multidimensional sensor array 116, the second multidimensional sensory array 118, the third multidimensional sensor array 120) is disposed at a different position for sensing biological data associated with a different thoracic region of the driver. As an illustrative example, the multidimensional sensor array 116 can be disposed at a position 412a proximate to an upper cervico-thoracic region 414a of the driver 402 and the second multidimensional sensor array 118 can be disposed at a position 412c proximate to an lower thoraco-lumbar region 414c of the driver 3402. Other numbers of multidimensional sensor arrays disposed in other positions or combinations of positions can also be implemented.

As discussed above in detail with FIG. 2, each of the plurality of sensors are provided at a position on the multidimensional sensor array to define a center of mass of the multidimensional array, where the center of mass is located external to an area bounded by the plurality of sensor. For example, in FIG. 2, the multidimensional array 200 has a center of mass 204 located external to an area bounded by the plurality of sensors. The sensors M1, M2, M3 and M4, which are mechanically coupled to the common structural coupling material 202, are provided (i.e., positioned) so as to define the center of mass 204 external to the area bounded by the plurality of sensors. Specifically, the center of mass 204 is located external to an area 206, which is bounded by the sensors M1, M2, M3 and M4. The area 206 is defined by a position of each of the plurality of sensors M1, M2, M3 and M4 and a geometric center 208 of the plurality of sensors M1, M2, M3 and M4. In one embodiment, the center of mass 204 is also defined by a weighted portion 210 of the multidimensional array 200. The weighted portion 210, in one embodiment, is implemented by a power source (not shown) positioned on the multidimensional array 200. In a further embodiment, the center of mass 204 is created by providing the multidimensional array in a curved shape configuration (not shown). By providing the center of mass 204 at a location external to the geometric center 208 of the plurality of sensors M1, M2, M3 and M4, the ambient mechanical vibration (i.e., noise) registers in each of the plurality of sensors M1, M2, M3 and M4, in plane (i.e., in phase) with respect to each other.

Referring again to FIG. 7, at step 704, the method includes selectively receiving an output from each of the plurality of sensors. For example, the filter 106 can include a multiplexor 115 configured to selectively receive an output (e.g., a raw data signal indicating a measurement of biological data associated with the driver) from each of the plurality of sensors M1, M2, M3 and M4. In one embodiment, the multiplexor 115 can selectively receive and/or obtain output from each of the plurality of sensors based on a predetermined factor. The predetermine factor can include, but is not limited to, a position of the multidimensional sensor array, a position of each sensor in the multidimensional array, a cluster associated with a sensor, a signal to noise ratio of the output of each sensor, among other factors.

At step 706, the method includes processing the output from each sensor of the plurality of sensors. In one embodiment, processing the output is based on clusters associated with each of the sensors. As can be seen in FIG. 6, the output signals Vm1, Vm2, Vm3 and Vm4 are processed (e.g., the filtering portion 604) based on clusters associated with each of the plurality of sensors in the multidimensional array. In particular, the acoustic sensors M2 and M3, which are associated with cluster 608, are connected to one half of an operational amplifier Amp1 via an RC couple R1 and C1. The output signals Vm2 and Vm3 are processed by the Amp 1. The output of the Amp1 is a summation of the output of M2 and M3, equal to Vm2+Vm3 filtered at 0.34-3.4 Hz.

In a further embodiment, processing the output from each sensor of the plurality of sensors is based on the positioning of each sensor. For example, processing the output can be based on a signal output from a sensor positioned along the X axis of the multidimensional array 200 and a signal output from a sensor position along the Y axis of the multidimensional array 200. This allows the moment arm from the X axis and the Y axis to become common mode during differential amplification. More specifically, the processing is based on signal output from a sensor positioned along the Y axis with a short and long moment arm and a sensor position along the X axis with an x moment arm on either side of the Y axis.

Similarly, the acoustic sensors M1 and M4, associated with the cluster 610, are also connected to one half of an operational amplifier Amp2 via an RC couple R1 and C1. The output signals Vm1 and Vm4 are processed by the Amp 2. The output of Amp2 is a summation of the output of M1, M4, equal to Vm1+Vm4 filtered at 0.34-3.4 Hz. Further, the output of each operational amplifier Amp1, Amp2 is fed to a differential bioinstrumentation amplifier Amp3 configured to deliver a gain of 5000/Rg=50000/10=5000 V/V. The Amp3 can provide noise cancellation of the output of the sensors M1, M2, M3 and M4. In particular, and as discussed above with FIG. 2, since the sensors M1, M2, M3 and M4 are mechanically coupled to a common structural coupling material 202, environmental vibrations impact each sensors M1, M2, M3 and M4 equally. Therefore, the Amp3 can remove the environmental vibrations from the output signal of each operational amplifier Amp1, Amp2, as a common mode. The output signal of the differential bioinstrumentation amplifier Amp3 is equal to GX[(Vm2+Vm3)−(Vm1+Vm4)] filtered.

Note that the paired sums Vm2+Vm3 and Vm1+Vm4 each contain sensor output from both a long moment arm noise component (Vm1, Vm3) and from a short arm moment arm (Vm2 and Vm4). Further, each paired sum contains sensor output from the out-of-phase rotational motion about the vertical axis. Thus, all noise components are common mode to the paired sums and cancel out on differential amplification.

The output signal of the differential bioinstrumentation amplifier Amp3 represents a biological signal that can be output to other systems and methods. Accordingly, at step 708, the method includes outputting a biological signal based on the processing. The biological signal that can be further analyzed (e.g., by the processor 104) to determine autonomic tone and a level of impairment of the driver 302. By providing a multidimensional array with a plurality of sensors mechanically coupled via a common structural coupling material and processing the output of the sensors based on regional differences, a high quality biological signal can be obtained and used to determine autonomic tone and a level impairment of the driver 302.

III. Exemplary Output

Figure 8:
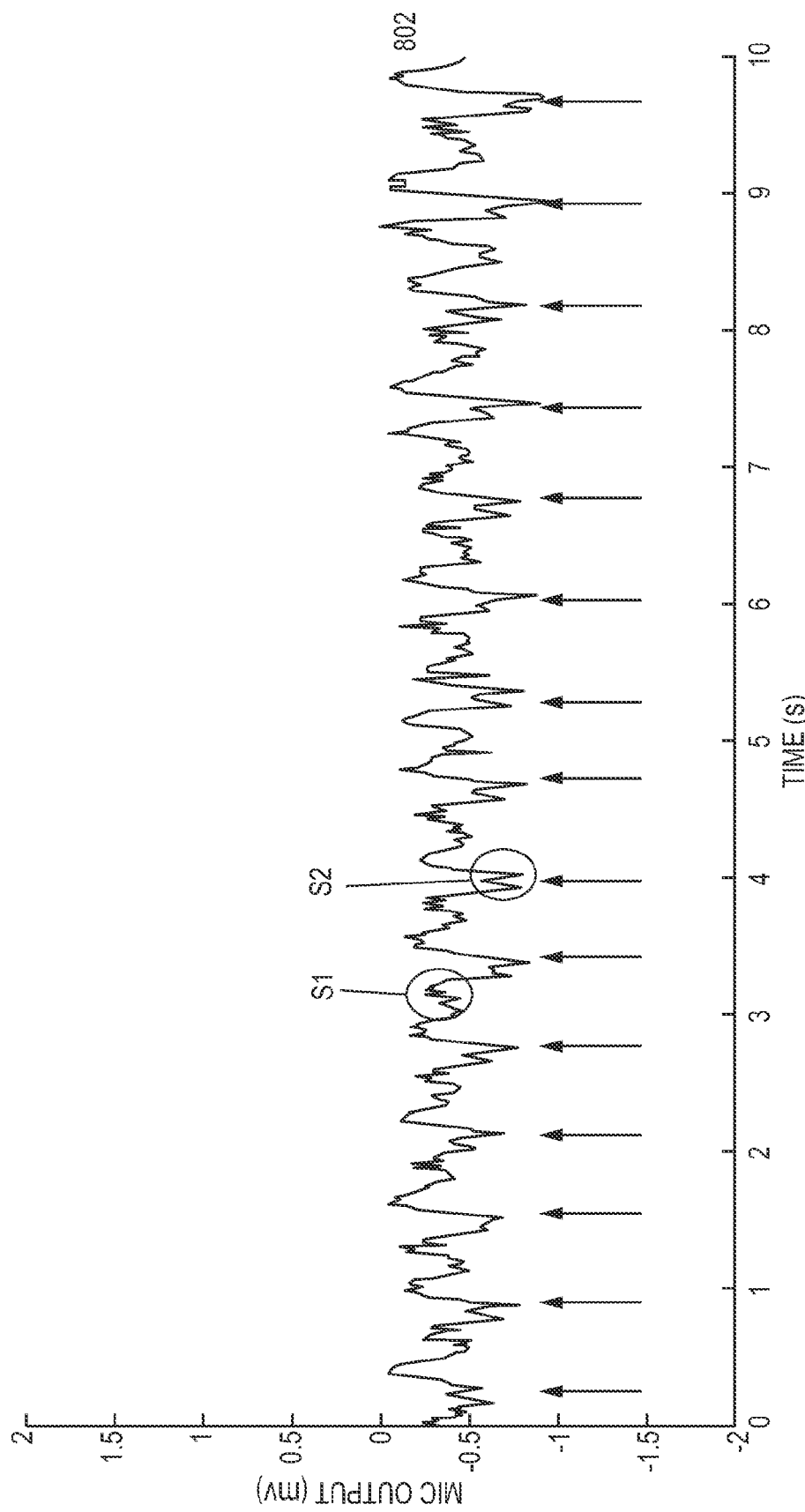
FIG. 8 is an example aortic flow wave output signal measured at an upper cervico-thoracic region and produced by the system of FIG. 1.

Exemplary outputs from the biological signal analysis system and other systems will now be described. These examples illustrated in FIGS. 8-10, 13-14 and 16 are discussed in the context of acoustic signals indicating biological data that are acquired and processed by the system 100 of FIG. 1 and with reference to the components of FIGS. 2-6. In particular, the acoustic signals indicate biological data associated with the heart and blood flow of an individual in a vehicle (e.g., a driver 302). Referring now to FIG. 8, an example aortic flow wave output signal 802 from the system 100 of FIG. 1 is shown. In particular the signal 802 is a biological signal output from a multidimensional sensor array 116 disposed at a position proximate to an upper cervico-thoracic region 414a of the driver 402. As can be seen in FIG. 8, conventional heart sounds S1 and S2 can be identified by the system 100. The peak aortic blood flow is detected by the wave troughs, which are indicated by arrows. Additionally, the output signal 802 has a dicrotic appearance (i.e., incisura) with notches at the vertices of the flow waves. These incisura are a manifestation of the sound S2 corresponding to the closure of the aortic and pulmonic valves.

Figure 9:
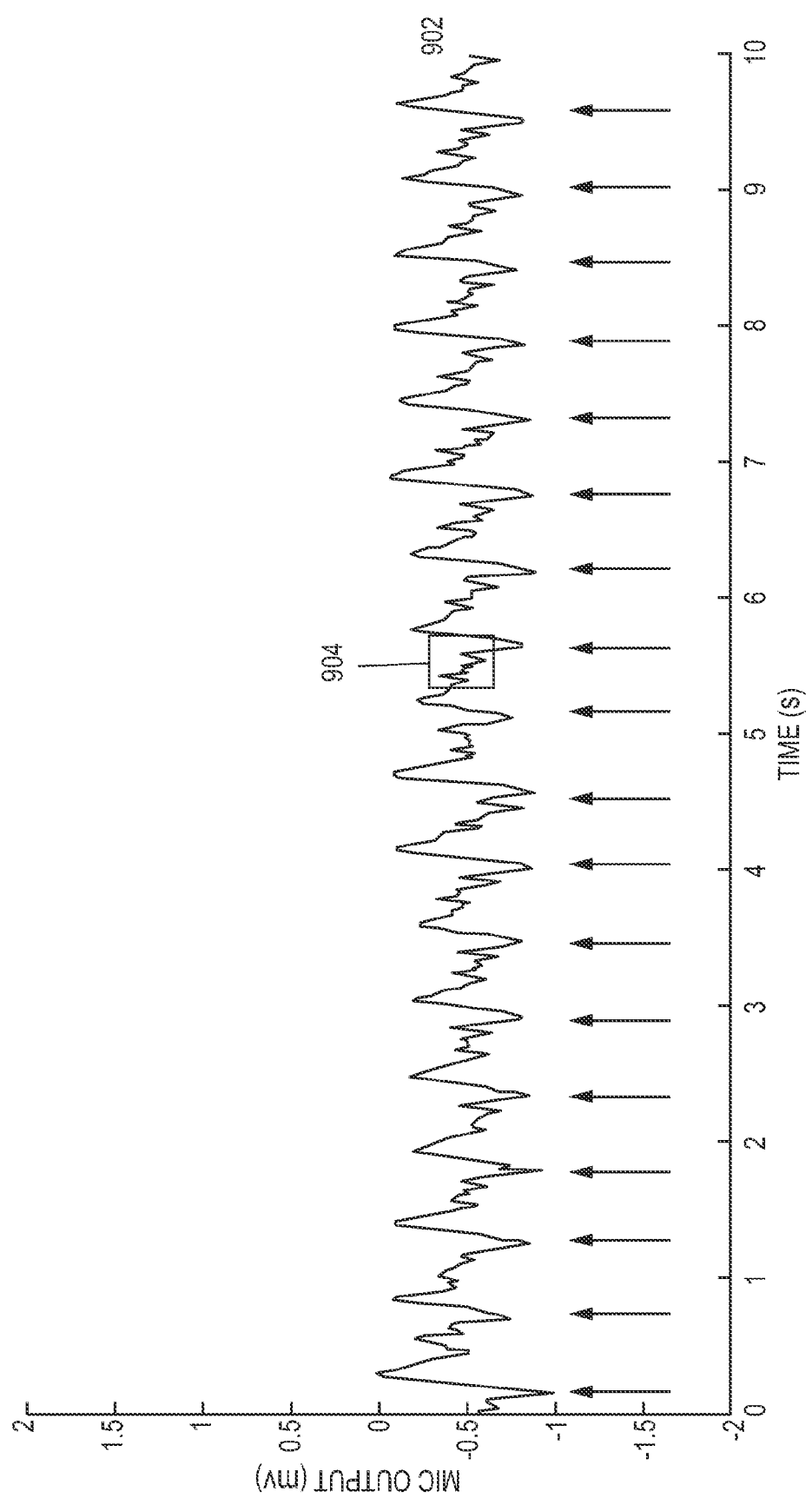
FIG. 9 is an example aortic flow wave output signal measured at a middle thoracic region and produced by the system of FIG. 1.
Figure 10:
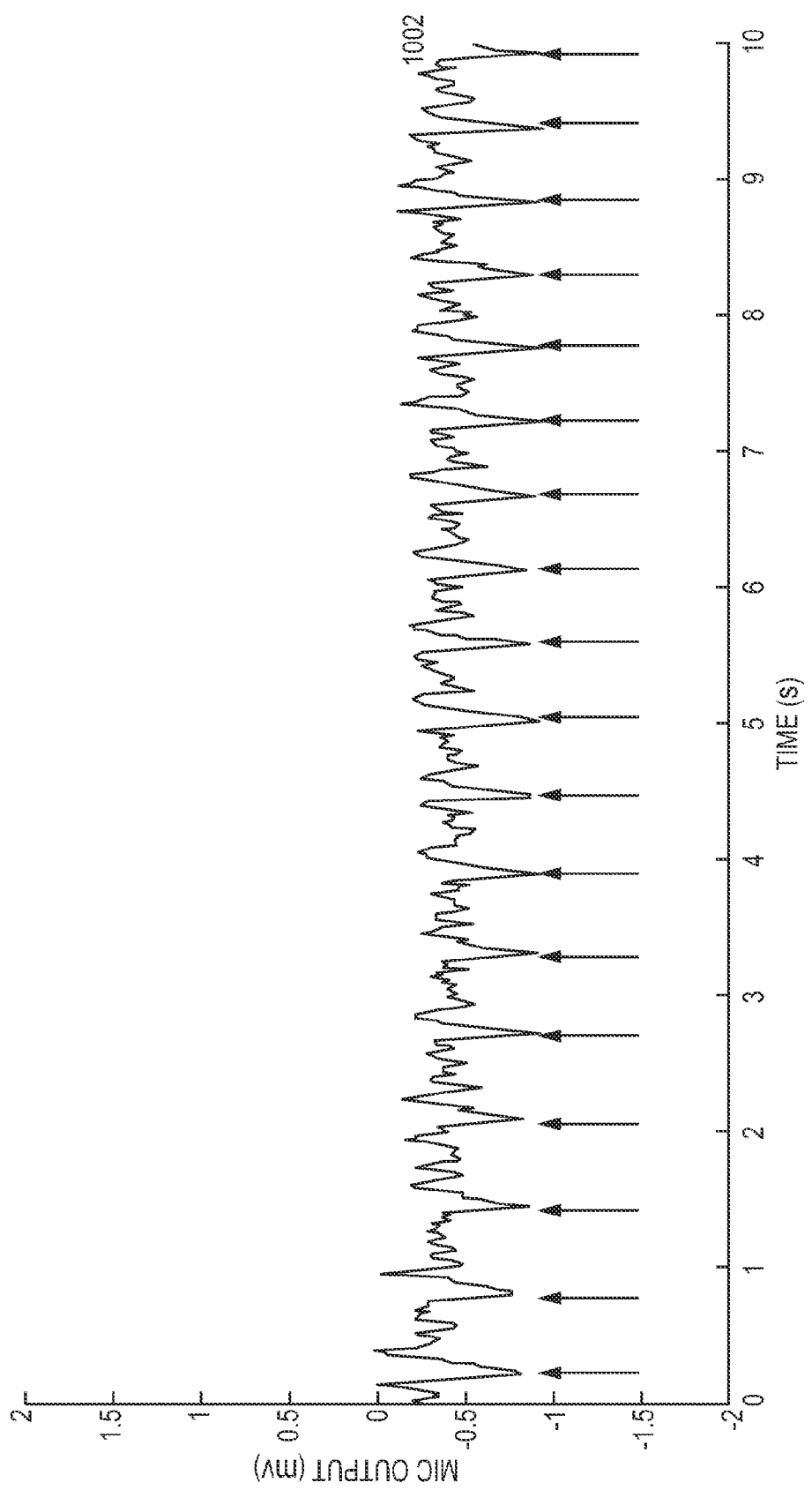
FIG. 10 is an example aortic flow wave output signal measured at a lower thoraco-lumbar region and produced by the system of FIG. 1.
Figure 11:
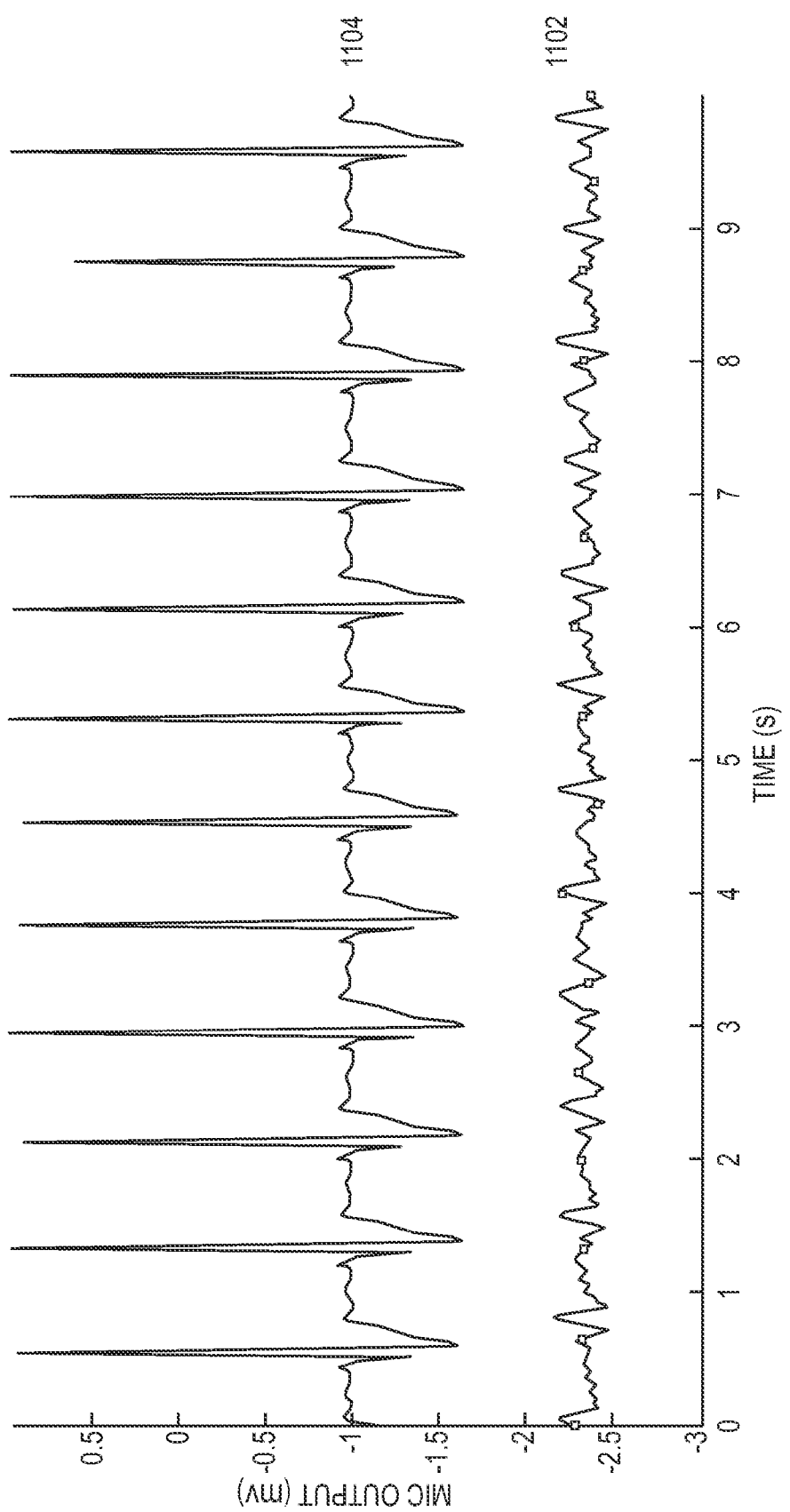
FIG. 11 is an example aortic flow wave output signal from a single sensor and a simultaneous EKG output signal in a car with a vehicle engine off.

FIG. 9 illustrates an example aortic flow wave output signal 802 output from a multidimensional sensor array 116 disposed at a position proximate to a middle thoracic region 414b of the driver 402. The dicrotic notch common to aortic pressure can be seen in the output signal 902 as indicated by numeral 904. Further, referring to FIG. 10, an example aortic flow wave output signal 1002 output from a multidimensional sensor array 116 disposed at a position proximate to a lower thoraco-lumbar region 414c of the driver 402. As is seen, the incisura is much less prominent in the signal 1002. At all regions (i.e., upper region, middle-region and lower-region), the peak aortic blood flow is detected by the wave troughs (i.e., as indicated by the arrows). These points can be used in applications that utilize interval calculations (e.g., R-R intervals) to estimate autonomic tone and an impairment state.

Figure 12:
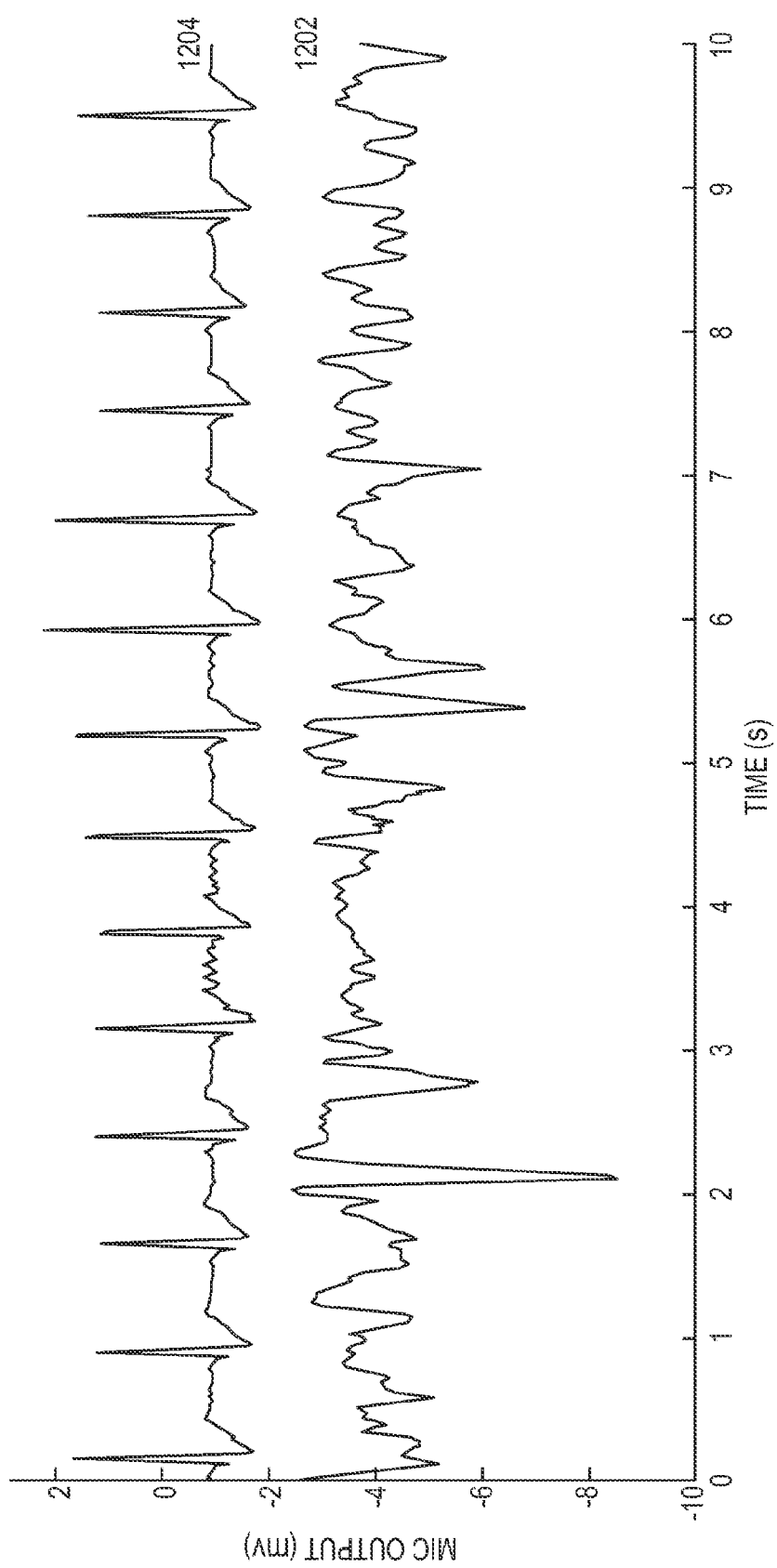
FIG. 12 is an example aortic flow wave output signal from a single sensor and a simultaneous EKG output signal measured in a vehicle with a vehicle engine running.

Referring now to FIGS. 11-16, exemplary output from a single sensor (i.e., not from the multidimensional array 116 of the system 100) as compared to an actual EKG are shown. Specifically, in FIG. 11, an example output signal 1102 from a single sensor (i.e., not from the multidimensional array 116 of the system 100) and an example output signal 1104 of a simultaneous EKG are shown. In FIG. 12, an example output signal 1202 from a single sensor (i.e., not from the multidimensional array 116 of the system 100) and an example output signal 1204 of a simultaneous EKG measured in a vehicle with the engine running are shown. The signals 1102 and 1202 are degraded from vehicle mechanical vibrations to the extent that the peaks in aortic blood flow can no longer be resolved.

Figure 13:
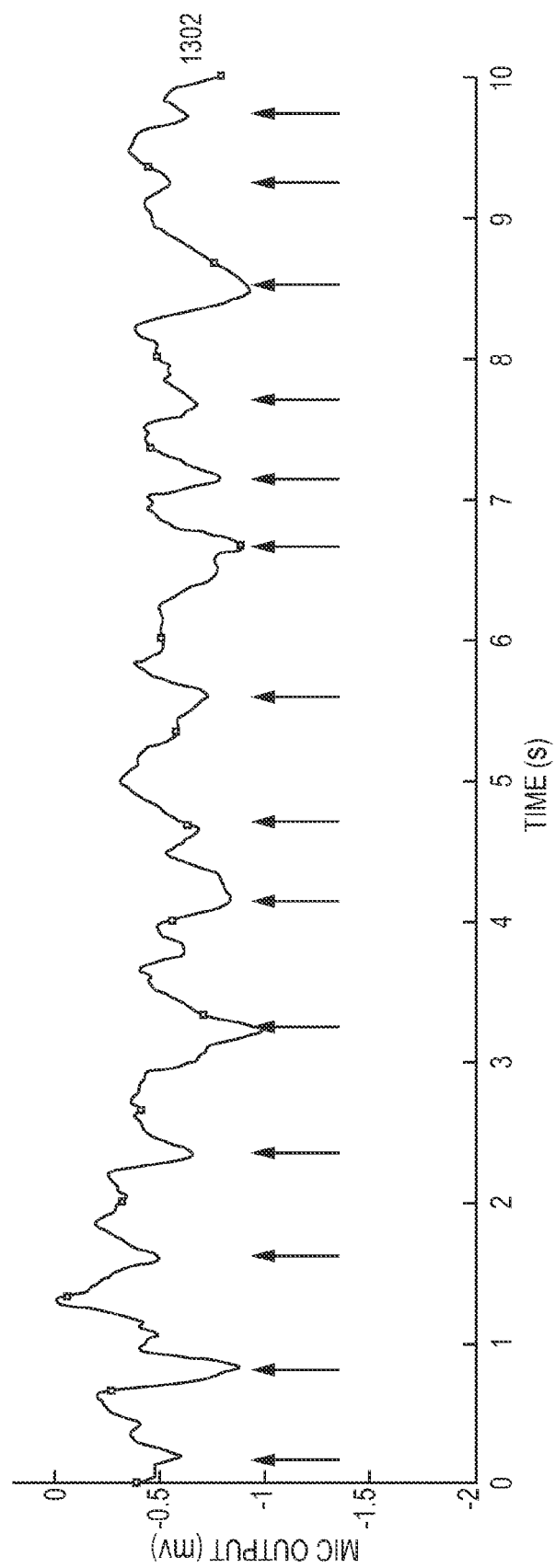
FIG. 13 is an example aortic flow wave output signal produced by the system of FIG. 1 and measured in a vehicle with a vehicle engine running.
Figure 14:
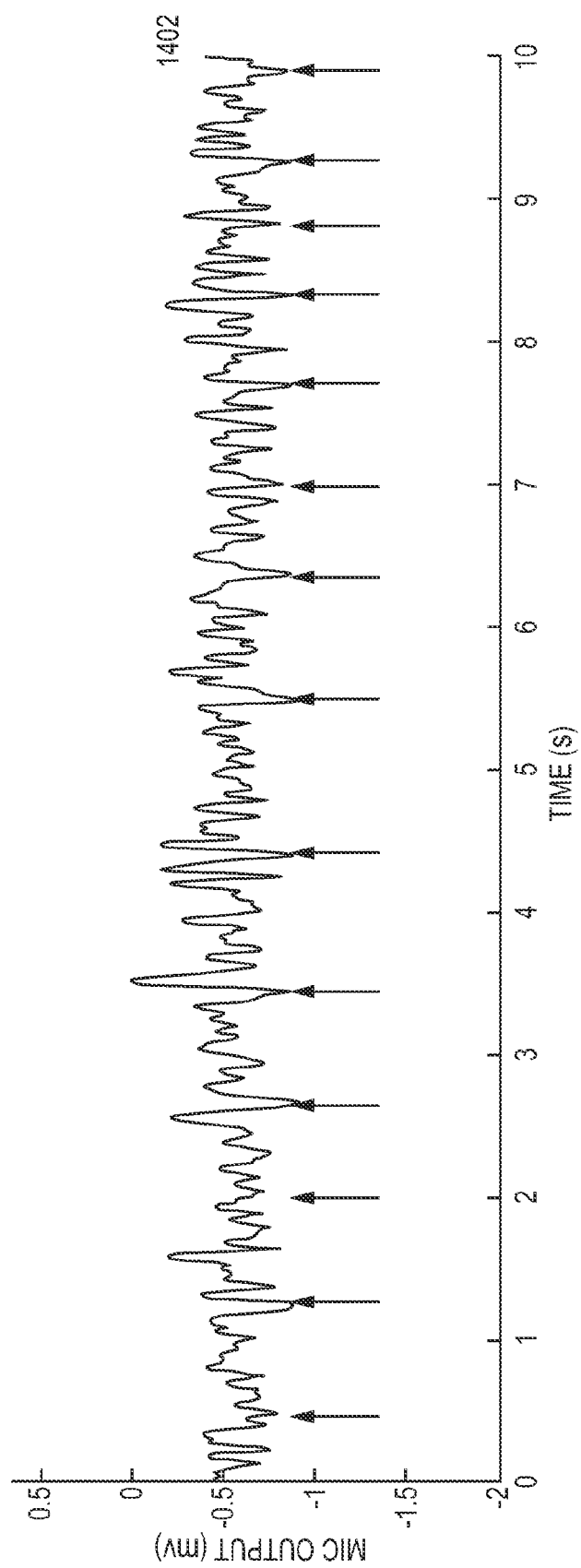
FIG. 14 is an example aortic flow wave output signal produced by the system of FIG. 1 and measured in a vehicle with a vehicle engine running and vehicle in motion.

In comparison, and with reference to FIGS. 13 and 14, example output from the multidimensional sensor array of the system 100 is shown. Specifically, FIG. 13, illustrates an output signal 1302 and FIG. 14 illustrates an output signal 1402. The mechanical coupling and differential amplification in the system 100 allows the heart rate of the driver to be resolved with the engine running. Specifically, the individual troughs corresponding to aortic blood flow (indicated by the arrows) are prominent and not have not been degraded by vehicle mechanical vibrations. Thus, by providing a multidimensional array with a plurality of sensors mechanically coupled via a common structural coupling material and processing the output of the sensors based on regional differences as discussed above with FIG. 1, a high quality biological signal can be obtained in a vehicle while the engine is running.

Figure 15:
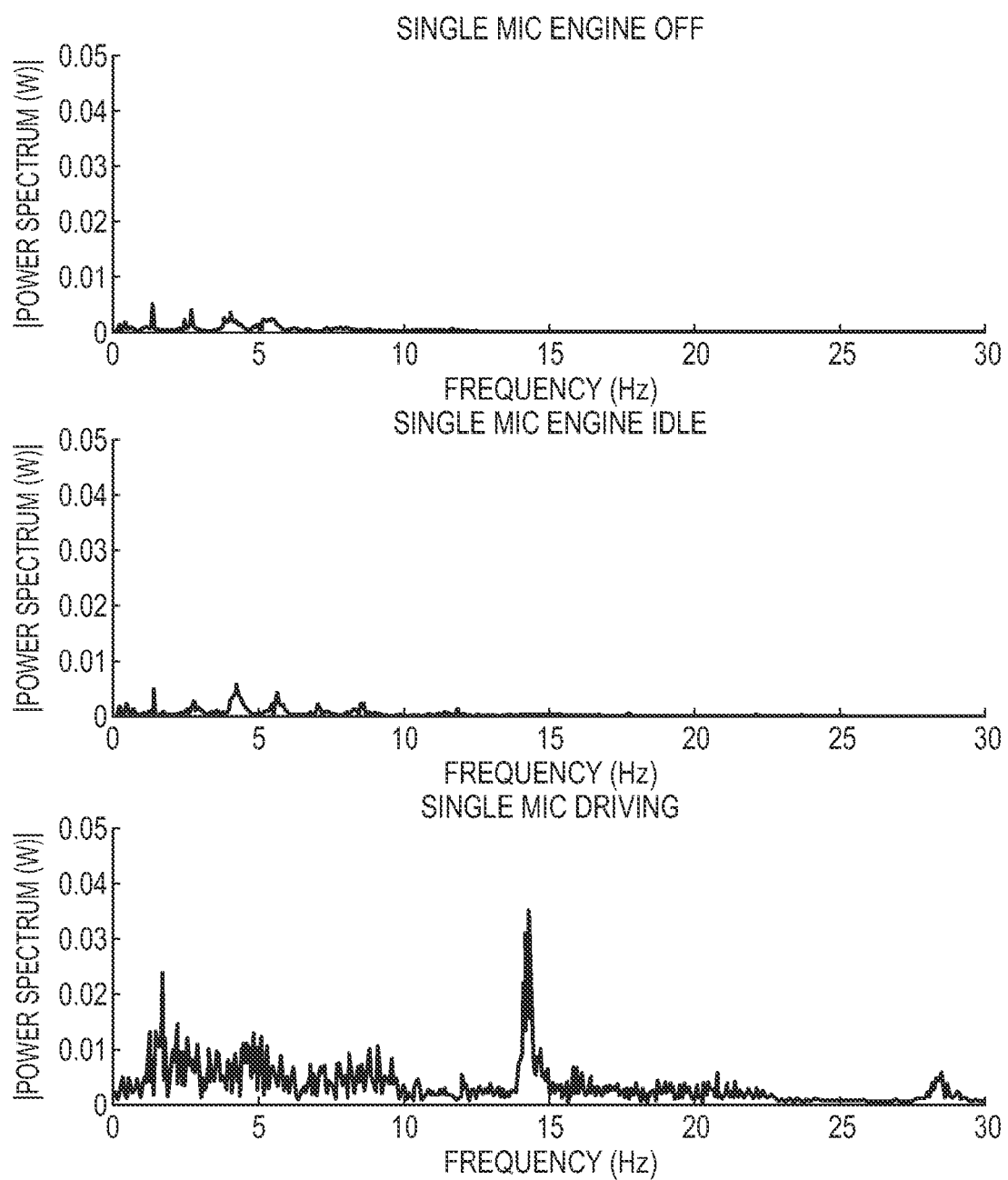
FIG. 15 is an example power spectrum output from a single sensor with the engine off, the engine idle and while driving.
Figure 16:
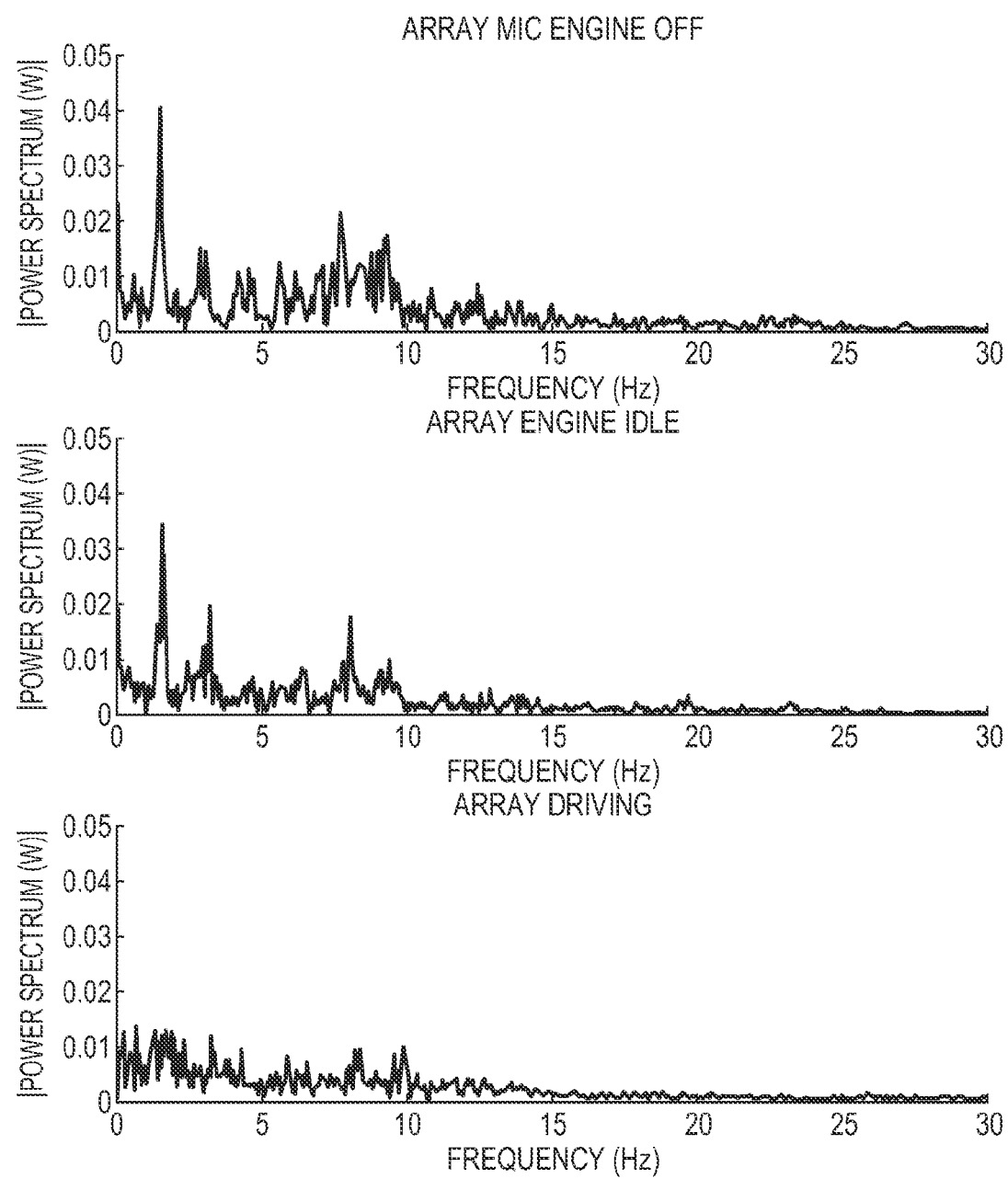
FIG. 16 is an example power spectrum output from the multidimensional array of FIG. 1 with the engine off, the engine idle and while driving.

Referring now to FIGS. 15 and 16, exemplary power spectrum output from a single sensor shown in FIG. 15 and exemplary power spectrum output from the multidimensional sensor array of the system 100 in FIG. 16 will be discussed. In FIG. 15, the output of a single sensor when the engine is off (top), the engine is idle (middle) and while driving (bottom) is shown. In FIG. 16, the output of the multidimensional array of FIGS. 1, 2, 3 and 6 is shown with the engine off (top), the engine idle (middle) and driving (bottom). Note the signal to noise ratio of the multidimensional array in FIG. 16 is about 8:1 the engine off and idling whereas in FIG. 15 it is just 3:1 with a single sensor. This observation illustrates the additive amplification benefit of using 4 sensors as opposed to just 1. Note when the engine is running is about 2:1 when using the array vs. 1:8 with just a single element (i.e., FIG. 15 bottom and FIG. 16 bottom). This observation illustrates the beneficial noise canceling effects of mechanical coupling. Thus, by mechanically coupling each of the plurality of sensors, the signal to noise ratio is improved while driving.

The embodiments discussed herein can also be described and implemented in the context of computer-readable storage medium storing computer-executable instructions. Computer-readable storage media includes computer storage media and communication media. For example, flash memory drives, digital versatile discs (DVDs), compact discs (CDs), floppy disks, and tape cassettes. Computer-readable storage media can include volatile and nonvolatile, removable and non-removable media implemented in any method or technology for storage of information such as computer readable instructions, data structures, modules or other data. Computer-readable storage media excludes non-transitory tangible media and propagated data signals.

It will be appreciated that various implementations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method for biological signal analysis, comprising:
providing a multidimensional sensor array disposed at a position for sensing biological data associated with a person, wherein the multidimensional sensor array includes a plurality of sensors, wherein each sensor of the plurality of sensors is mechanically coupled to a common structural coupling material;
selectively receiving an output from each sensor of the plurality of sensors;
processing the output from each sensor of the plurality of sensors; and
outputting a biological signal based on the processing, wherein each of the plurality of sensors are provided at a position on the multidimensional sensor array to define a center of mass of the multidimensional sensor array external to an area bounded by the plurality of sensors, wherein an ambient mechanical vibration registers in each sensor of the plurality of sensors in a plane with respect to another sensor of the plurality of sensors based on the center of mass of the multidimensional sensor array being external to the area bounded by the plurality of sensors.

2. The method of claim 1, wherein the center of mass of the multidimensional sensor array is defined by a weighted portion of the multidimensional sensor array.

3. The method of claim 1, wherein processing the output from each sensor is based on a cluster associated with each sensor.

4. The method of claim 1, wherein the position for sensing biological data is proximate to a thoracic region of the person.

5. The method of claim 4, wherein the thoracic region is one of an upper cervico-thoracic region, a middle thoracic region or a lower thoraco-lumbar region.

6. The method of claim 1, wherein providing the multidimensional sensor array further includes providing more than one multidimensional sensor array, wherein each multidimensional sensor array is disposed at a different position for sensing biological data.

7. A system for biological signal analysis, comprising:
a multidimensional sensor array disposed at a position for sensing biological data associated with a person, wherein the multidimensional sensor array includes a plurality of sensors, wherein each sensor of the plurality of sensors is mechanically coupled to a common structural coupling material; and
a filter for selectively receiving an output from each of the plurality of sensors, processing the output from each of the plurality of sensors and outputting a biological signal based on the processing, wherein each of the plurality of sensors are provided at a position on the multidimensional sensor array to define a center of mass of the multidimensional sensor array external to an area bounded by the plurality of sensors, wherein an ambient mechanical vibration registers in each sensor of the plurality of sensors in a plane with respect to another sensor of the plurality of sensors based on the center of mass of the multidimensional sensor array being external to the area bounded by the plurality of sensors.

8. The system of claim 7, wherein the center of mass of the multidimensional sensor array is defined by a weighted portion of the multidimensional sensor array.

9. The system of claim 7, wherein processing the output from each sensor is based on a cluster associated with each sensor.

10. The system of claim 7, wherein the filter further includes a multiplexor for selectively receiving the output from each of the plurality of sensors.

11. The system of claim 7, wherein the multidimensional sensor array is disposed at a position for sensing biological data associated with a thoracic region of the person.

12. The system of claim 11, further including more than one multidimensional sensor array, wherein each multidimensional sensor array is disposed at a different position for sensing biological data associated with a different thoracic region of the person.

13. The system of claim 12, wherein the filter further includes a multiplexor for selectively receiving the output from each of the plurality of sensors based on the position of the multidimensional sensor array.

14. A non-transitory computer-readable storage medium storing instructions that, when executed by a computer, causes the computer to perform a method, the method comprising:
receiving an output from a multidimensional sensor array that is disposed in a position for sensing biological data associated with a person, wherein the multidimensional sensor array includes a plurality of sensors and a center of mass of the multidimensional sensor array is located external to a geometric center defined by the plurality of sensors, wherein each sensor of the plurality of sensors is mechanically coupled to a common structural coupling material;
selectively forwarding an output from each sensor of the plurality of sensors for processing;
processing the output based from each sensor of the plurality of sensors; and
outputting a biological signal based on the processing.

15. The non-transitory computer-readable medium of claim 14, wherein the processing further includes selectively filtering the output based on a cluster associated with each sensor.

16. The non-transitory computer-readable medium of claim 15, wherein selectively forwarding an output from each sensor of the plurality of sensors is based on the position of the multidimensional sensor array.

17. A multidimensional sensor arrangement for biological Signal analysis, comprising:
a plurality of sensors, wherein a center of mass of the multidimensional sensor arrangement is located external to a geometric center defined by the plurality of sensors;
a common structural coupling material upon which each sensor of the plurality of sensors is mechanically fixed; and
a filter operatively connected to the plurality of sensors, the filter configured to selectively receive output from each of the plurality of sensors and process the output, thereby outputting a biological signal.

18. The multidimensional sensor arrangement of claim 17, wherein the multidimensional sensor arrangement is disposed at a position for sensing biological data associated with a person.

19. The multidimensional sensor arrangement of claim 17, wherein the filter is further configured to process the output based on a cluster associated with each sensor.

* * * * *